(12) United States Patent
Simpson

(10) Patent No.: US 6,309,385 B1
(45) Date of Patent: Oct. 30, 2001

(54) ELECTRODE HAVING COMPOSITION-MATCHED, COMMON-LEAD THERMOCOUPLE WIRE FOR PROVIDING MULTIPLE TEMPERATURE-SENSITIVE JUNCTIONS

(75) Inventor: John A. Simpson, Carlsbad, CA (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

(21) Appl. No.: 09/502,179

(22) Filed: Feb. 10, 2000

Related U.S. Application Data

(62) Division of application No. 09/072,801, filed on May 5, 1998, now Pat. No. 6,042,580.

(51) Int. Cl.$^7$ .................................................. A61B 18/04
(52) U.S. Cl. ................................ 606/32; 606/41; 607/101
(58) Field of Search .................................. 606/31–35, 41, 606/42, 45–50; 607/101, 102, 122; 600/549

(56) References Cited

U.S. PATENT DOCUMENTS 4,966,597   10/1990   Cosman .................................. 606/50

FOREIGN PATENT DOCUMENTS

WO93/13816   7/1993   (WO) .
WO96/00036   1/1996   (WO) .

OTHER PUBLICATIONS

ISHM '87 Proceedings "Taming Thermocouple Voltages in Microelectronics" by Roy Chapel, pp. 104–112.
"The Thermocouple", Omega Catalog, vol. 27, pp. Z9–Z20.

*Primary Examiner*—Roy Gibson
(74) *Attorney, Agent, or Firm*—Fulwider Patton Lee & Utecht, LLP

(57) ABSTRACT

An apparatus for providing a plurality of signals, each indicative of a temperature at an individual location on an electrode which is formed of a first metallic material includes a plurality of electrically conductive sensor leads, each individually connected to the electrode to form a sensor junction. Each sensor junction has a temperature-dependent voltage associated with it. An electrically conductive common lead is connected to the electrode to form a common junction. The common lead is formed of a second metallic material such that substantially no temperature-dependent voltage is associated with the common junction. Each of the sensor leads is formed of a metallic material different than the first metallic material. Each metallic material has a known Seebeck coefficient relative to the first metallic material. The ratio of the magnitude of the Seebeck coefficient of the sensor lead metallic material relative to the first metallic material and the magnitude of the Seebeck coefficient of the common lead metallic material relative to the first metallic material is at least ten to one. The common lead generally exhibits a thermoelectric output similar to the first metallic material and may be formed of the first metallic material.

24 Claims, 14 Drawing Sheets

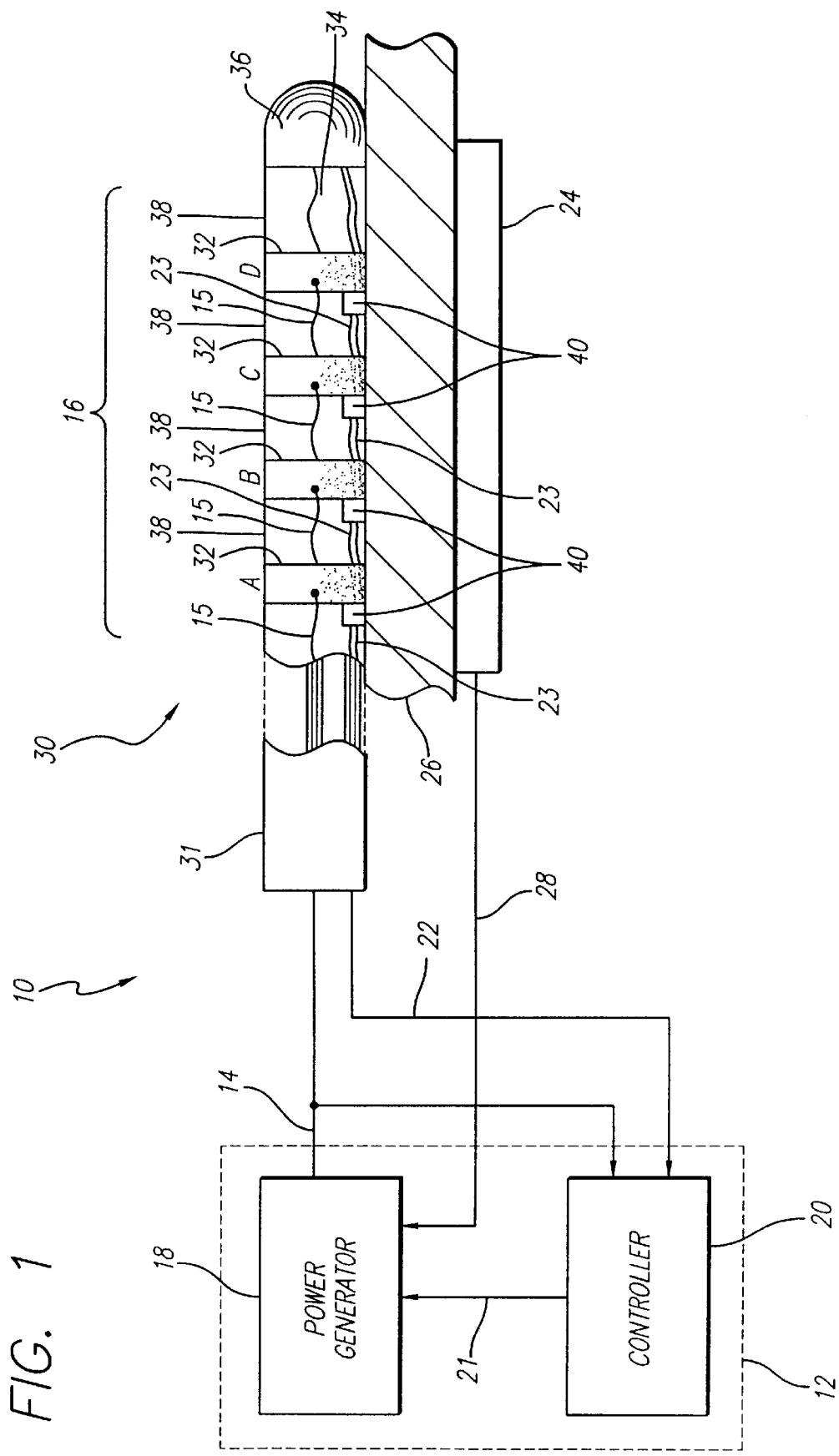

FIG. 4
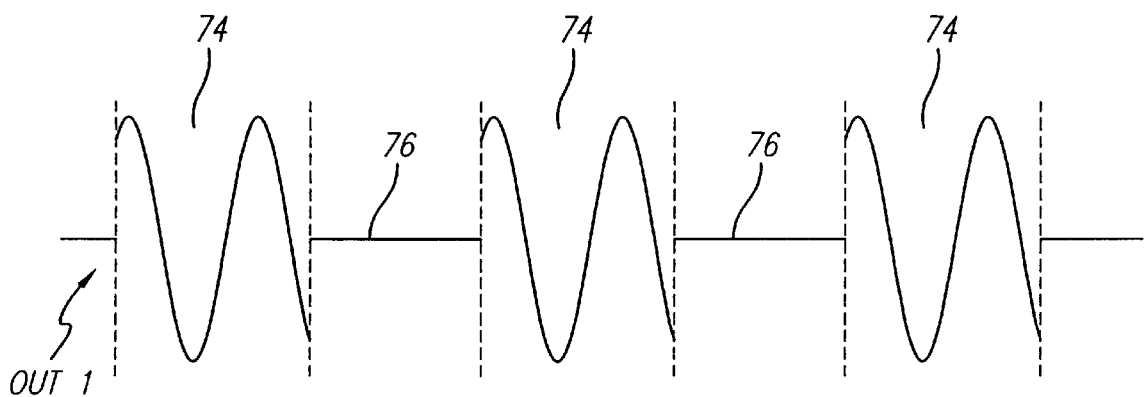
FIG. 5
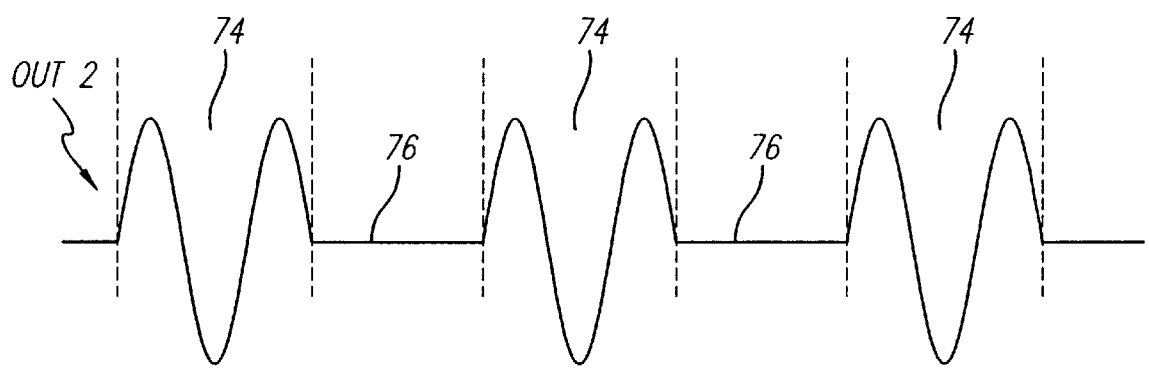
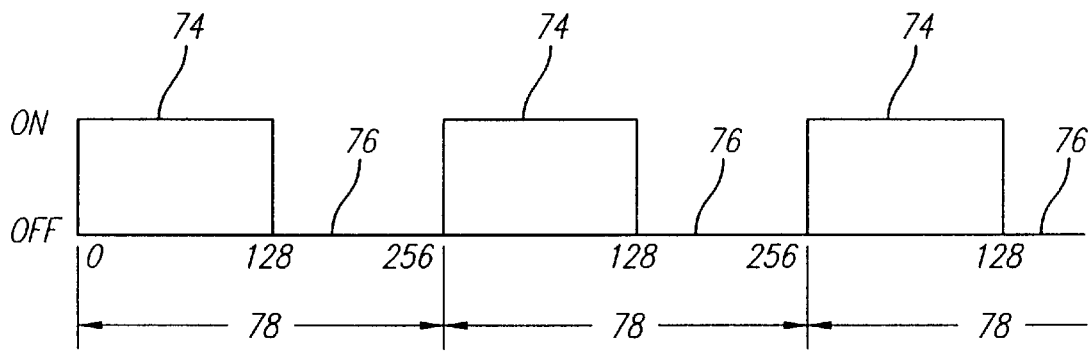
FIG. 6

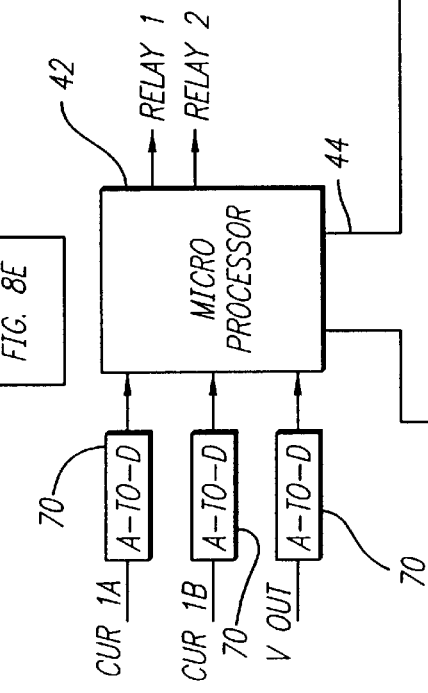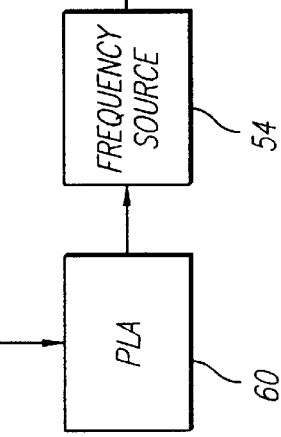
FIG. 8A
FIG. 8B

ELECTRODE HAVING COMPOSITION-MATCHED, COMMON-LEAD THERMOCOUPLE WIRE FOR PROVIDING MULTIPLE TEMPERATURE-SENSITIVE JUNCTIONS

RELATED APPLICATIONS

This is a division of co-pending application Ser. No. 09/072,801, filed May 5, 1998 now U.S. Pat. No. 6,042,580.

BACKGROUND OF THE INVENTION

The invention relates generally to an electrophysiological ("EP") apparatus and method for providing energy to biological tissue, and more particularly, to an electrode with a composition-matched, common-lead thermocouple wire for providing multiple temperature-sensitive junctions on the electrode.

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of, or damage to, the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed by percutaneous ablation, a procedure in which a catheter is percutaneously introduced into the patient and directed through an artery to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or create a conductive tissue block to restore normal heart beat or at least an improved heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of atrial fibrillation ("AF"), a procedure published by Cox et al. and known as the "Maze procedure" involves continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate EP catheter system.

There are two general methods of applying RF energy to cardiac tissue, unipolar and bipolar. In the unipolar method a large surface area electrode; e.g., a backplate, is placed on the chest, back or other external location of the patient to serve as a return. The backplate completes an electrical circuit with one or more electrodes that are introduced into the heart, usually via a catheter, and placed in intimate contact with the aberrant conductive tissue. In the bipolar method, electrodes introduced into the heart have different potentials and complete an electrical circuit between themselves. In the bipolar method, the flux traveling between the two electrodes of the catheter enters the tissue to cause ablation.

During ablation, the electrodes are placed in intimate contact with the target endocardial tissue. RF energy is applied to the electrodes to raise the temperature of the target tissue to a non-viable state. In general, the temperature boundary between viable and non-viable tissue is approximately 48° Centigrade. Tissue heated to a temperature above 48° C. becomes non-viable and defines the ablation volume. The objective is to elevate the tissue temperature, which is generally at 37° C., fairly uniformly to an ablation temperature above 48° C., while keeping both the temperature at the tissue surface and the temperature of the electrode below 100° C.

During ablation, portions of the electrodes are typically in contact with the blood, so that it is possible for clotting and boiling of blood to occur if those electrodes reach an excessive temperature. Both of these conditions are undesirable. Clotting is particularly troublesome at the surface of the catheter electrode because the impedance at the electrode rises to a level where the power delivery is insufficient to effect ablation. The catheter must be removed and cleaned before the procedure can continue. Additionally, too great a rise in impedance can result in sparking and thrombus formation within the heart, both of which are also undesirable.

Further, too great a temperature at the interface between the electrode and the tissue can cause the tissue to reach a high impedance which will attenuate and even block the further transmission of RF energy into the tissue thereby interfering with ablation of tissue at that location.

Even though no significant amount of heat is generated in the electrodes themselves, adjacent heated endocardial tissue heats the electrodes via heat conduction through the tissue. As mentioned above, part of the active electrode will be in contact with the blood in the heart and if the electrode temperature exceeds 90–100°, it can result in blood boiling and clotting on the electrode. The application of RF energy must then be stopped. However, shutting the RF generator off due to the temperature rise may not allow sufficient time to complete the entire ablation procedure. Providing an ablation electrode capable of applying higher amounts of power for a longer period of time to ablate the damaged tissue to an acceptable depth is a goal of current ablation catheter electrode design. It has been found that higher power for longer time periods results in a higher probability of success of the ablation procedure.

To avoid clotting and blood boiling, RF ablation catheters for cardiac applications typically provide temperature feedback during ablation via a temperature sensor such as a thermocouple. In its simplest form, a thermocouple consists of two dissimilar metals joined together at one end called a "bead" or junction, such as a conventional copper/constantan type "T" thermocouple. When the junction is heated a thermoelectric potential arises and can be measured across the unconnected ends. This is also known as the thermoelectric or Seebeck effect. This voltage is proportional to the temperature difference between the junction and the non-joined ends.

A conventional RF ablation catheter typically has a single tip electrode and a single temperature sensor mounted along the centerline of the tip electrode where temperature readings are not affected by the rotational orientation of the catheter. Although a temperature gradient typically exists in tip electrodes, wherein the electrode is hottest at the tissue interface and coolest on the opposite side which is in contact with circulating blood, the centerline sensor provides a moderate output by which it can be determined whether the temperature of the tissue contacted by the electrode is being raised sufficiently, and whether a therapeutic lesion is being generated.

In the case where a catheter has a band electrode, such as for the treatment of atrial fibrillation by the ablation of tissue, a single temperature sensor mounted to the band may not provide the temperature of the tissue contacting the band electrode. Typically the side of the band which is in direct contact with the tissue becomes significantly hotter than the rest of the band electrode that is cooled by the blood flow. Thus, the temperature reading can be dramatically influenced by the rotational orientation of the catheter during RF ablation. If the band is oriented so that the single temperature sensor is not in contact with the tissue during the application of ablation energy, not only would there be a time lag in the sensor reaching the tissue temperature, but due to the effect of the cooling blood flow, the sensor reading may never approach the actual tissue temperature.

To overcome the effect that the rotation orientation of the band electrode has on temperature sensing, two thermocouples, positioned at different locations of the band electrode, may be used. A theory is that having a sensor in contact with tissue is more likely. While attachment of multiple temperature sensors to the band electrode can result in a higher probability of sensing the actual tissue interface temperature, this also increases the number of wires occupying space within the catheter. As is well appreciated by those skilled in the art, an increase in the number of internal wires could mean an undesirable increase in catheter diameter to accommodate those wires. Conventional types of thermocouples each require a thermocouple wire pair. Two thermocouples at each band electrode would result in four wires per band electrode so that the use of multiple temperature sensors may not be practical, particularly where the catheter carries multiple band electrodes that require temperature monitoring.

The larger the catheter, the more traumatic it is to the patient. Also, the more difficult it may be to negotiate the patient's vessels to position the catheter at the desired location in the heart. It is desirable to provide a catheter with as small a diameter as possible. A limiting factor in reducing the size of the catheter is the amount of devices and leads that must be carried inside the catheter. In the case of a catheter having ten band electrodes with two thermocouple temperature sensors at each electrode, a total of fifty wires would be necessary; one power wire for each electrode and two wires for each thermocouple. The size of fifty wires inside a catheter can be significant, causing an increased diameter of the catheter. Yet it is desirable to retain the electrodes and the associated temperature sensors so that more precise control over the energy applied to the biological tissue can be effected. Thus, it would be desirable to reduce the number of wires within a catheter, yet retain the same functionality.

Hence, those skilled in the art have recognized a need for providing an electrode with multiple temperature-sensitive junctions for providing temperature readings at a plurality of locations on the electrode but with a reduced number of sensor leads. Similarly, a need has been recognized for a method for providing temperature readings at a plurality of locations on an electrode using a reduced number of sensor leads The invention fulfills these needs and others.

SUMMARY OF THE INVENTION

Briefly, and in general terms, the invention is directed to an apparatus and a method for sensing temperature at multiple locations on an electrode using a reduced number of temperature sensor leads In one aspect, the invention comprises an apparatus for providing a plurality of signals, each indicative of a temperature at an individual location on an electrode which is formed of a first metallic material. The apparatus includes a plurality of electrically conductive sensor leads, each individually connected to the electrode to form a sensor junction. Each sensor junction has a temperature-dependent voltage associated with it. The apparatus also includes an electrically conductive common lead connected to the electrode to form a common junction. The common lead is formed of a second metallic material such that substantially no temperature-dependent voltage is associated with the common junction.

By selecting the second metallic material such that the temperature-dependent voltage at the common junction is substantially zero, the present invention allows for the measurement of a temperature-dependent voltage at a plurality of distinct points on the electrode. This in turn allows for the determination of the temperature at a plurality of distinct points on the electrode, using only N+1 electrically conductive members (where N equals the number of distinct points). This number of conductive members is significantly less than the two wires per distinct point of measurement typically required in prior art. Thus the number of wires required to fit in a device using the electrode is reduced, thereby allowing for a reduction in device size.

In a more detailed aspect of the invention, each of the sensor leads is formed of a metallic material different than the first metallic material. Each metallic material has a known Seebeck coefficient relative to the first metallic material. In another detailed aspect the ratio of the magnitude of the Seebeck coefficient of the sensor lead metallic material relative to the first metallic material and the magnitude of the Seebeck coefficient of the common lead metallic material relative to the first metallic material is at least ten to one In a further detailed aspect, the common lead is formed of the first metallic material. In yet another aspect, the first metallic material is substantially pure platinum.

In yet another aspect, the invention includes a method for monitoring the temperature at a plurality of locations on an electrode which is formed of a first metallic material. The method includes the step of connecting a plurality of electrically conductive sensor leads to the electrode to form a plurality of sensor junctions, each having a temperature-dependent voltage associated with it. Also included is the step of connecting an electrically conductive common lead to the electrode to form a common junction which also has a temperature-dependent voltage associated with it. The common lead is formed of a second metallic material such that the temperature-dependent voltage at the common junction is substantially zero. Also included are the steps of, for each sensor lead, measuring the voltage between the sensor lead and the common lead and, for each measured voltage, converting the measured voltage to a temperature value.

These and other aspects and advantages of the invention will become apparent from the following detailed description and the accompanying drawings, which illustrate by way of example the features of the invention.

BRIEF DESCRIPTION OF THE DRAWINGS

FIG. 1 is a schematic diagram of an ablation apparatus including a power control system, electrode device and backplate;

FIGS. 2-1 and 2-2 form a block diagram presenting more detail of a power control system in accordance with aspects of the invention, showing phase angle control, duty cycle control, and impedance and temperature monitoring;

FIG. 4 depicts a first power waveform having a first phase angle and alternating instances of peak power and very low power;

FIG. 5 depicts a second power waveform having a second phase angle different from the first phase angle and alternating instances of peak power and very low power;

FIG. 6 presents a time frame (TF) diagram showing a fifty-percent duty cycle;

FIGS. 8A, 8B, 8C, 8D, and 8E are schematic diagrams of an embodiment of a power control system in accordance with aspects of the invention with FIG. 8A showing how FIGS. 8B, 8C, 8D and 8E are related;

DETAILED DESCRIPTION OF PREFERRED EMBODIMENTS

Figures 1, 2:
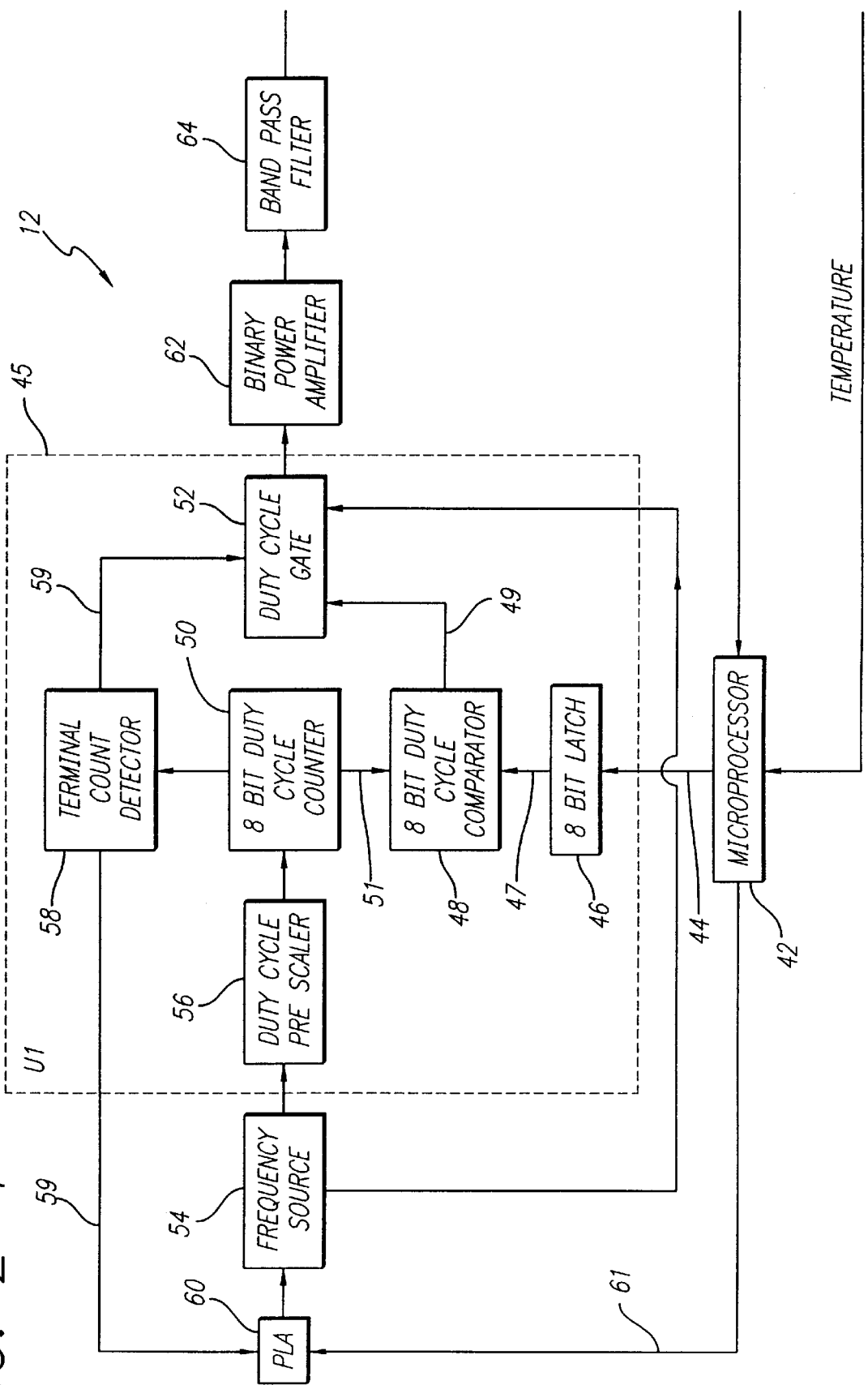
Figure 2:
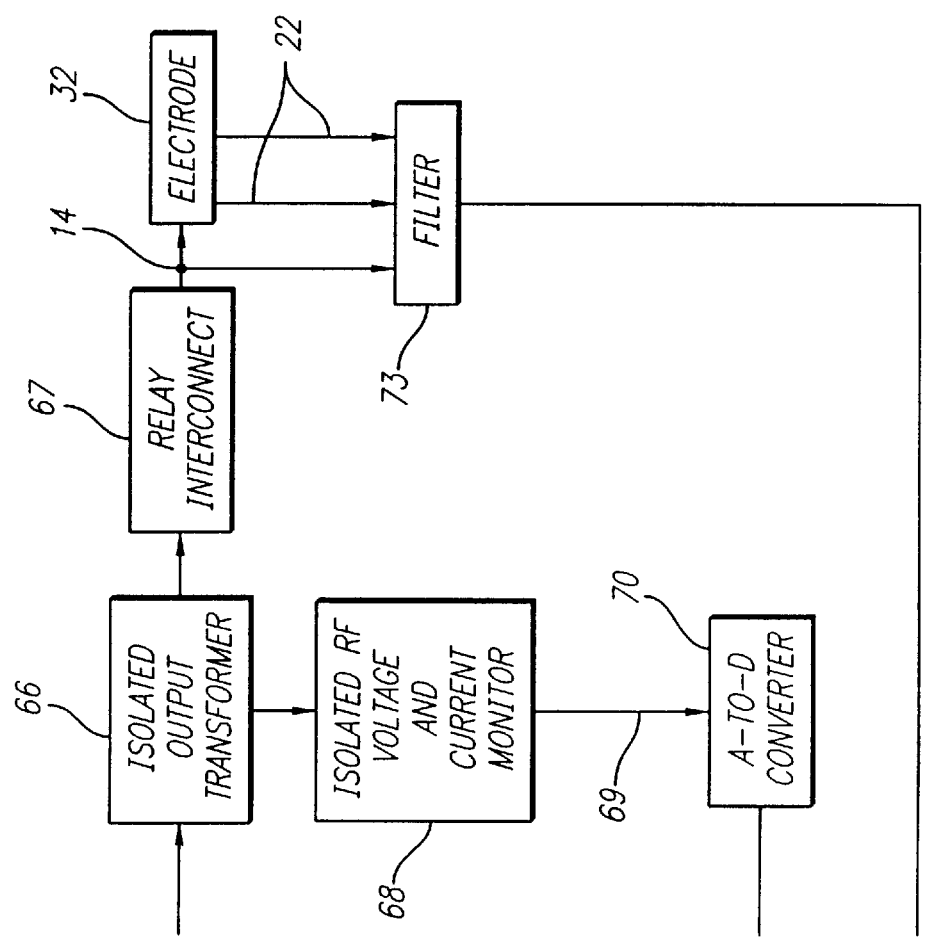

Turning now to the drawings, in which like reference numerals are used to designate like or corresponding elements among the several figures, in FIG. 1 there is shown an ablation apparatus 10 in accordance with aspects of the present invention. The apparatus 10 includes a power control system 12 that provides power or drive 14 to an electrode device 16. The power control system 12 comprises a power generator 18 that may have any number of output channels through which it provides the power 14. The operation of the power generator 18 is controlled by a controller 20 which outputs control signals 21 to the power generator 18. The controller 20 monitors the power 14 provided by the power generator 18. In addition, the controller 20 also receives temperature signals 22 from the electrode device 16. Based on the power 14 and temperature signals 22 the controller 20 adjusts the operation of the power generator 18. A backplate 24 is located proximal to the biological site 26 opposite the site from the electrode device 16, and is connected by a backplate wire 28 to the power generator 18. The backplate 24 is set at the reference level to the power provided to the electrodes, as discussed in detail below.

The electrode device 16 is typically part of a steerable EP catheter 30 capable of being percutaneously introduced into a biological site 26, e.g., the atrium or ventricle of the heart. The electrode device 16 is shown in schematic form with the components drawn to more clearly illustrate the relationship between the components and the relationship between the components and the power control system 12. In this embodiment, the catheter 30 comprises a distal segment 34 and a handle 31 located outside the patient. A preferred embodiment of the electrode device 16 includes twelve band electrodes 32 arranged in a substantially linear array along the distal segment 34 of the catheter 30. The electrode device 16 may include a tip electrode 36. (For clarity of illustration, only four band electrodes 32 are shown in the figures although as stated, a preferred embodiment may include many more.) The band electrodes 32 are arranged so that there is space 38 between adjacent electrodes. In one configuration of the electrode device 16, the width of the band electrodes 32 is 3 mm and the space 38 between the electrodes is 4 mm. The total length of the electrode device 16, as such, is approximately 8 cm.

The arrangement of the band electrodes 32 is not limited to a linear array and may take the form of other patterns. A substantially linear array is preferred for certain therapeutic procedures, such as treatment of atrial fibrillation, in which linear lesions of typically 4 to 8 cm in length are desired. A linear array is more easily carried by the catheter 30 and also lessens the size of the catheter.

The band electrodes 32 are formed of a material having a significantly higher thermal conductivity than that of the biological tissue 26. Possible materials include silver, gold, chromium, aluminum, molybdenum, tungsten, nickel, platinum, and platinum/10% iridium. Because of the difference in thermal conductivity between the electrodes 32 and the tissue 26, the electrodes 32 cool off more rapidly in the flowing fluids at the biological site. The power supplied to the electrodes 32 may be adjusted during ablation to allow for the cooling of the electrodes while at the same time allowing for the temperature of the tissue to build up so that ablation results. The electrodes 32 are sized so that the surface area available for contact with fluid in the heart, e.g., blood, is sufficient to allow for efficient heat dissipation from the electrodes to the surrounding blood. In a preferred embodiment, the electrodes 32 are 7 French (2.3 mm in diameter) with a length of 3 mm.

The thickness of the band electrodes 32 also affects the ability of the electrode to draw thermal energy away from the tissue it contacts. In the present embodiment, the electrodes 32 are kept substantially thin so that the electrodes effectively draw energy away from the tissue without having to unduly increase the outer diameter of the electrode. In a preferred embodiment of the invention, the thickness of the band electrodes is 0.05 to 0.13 mm (0.002 to 0.005 inches).

Associated with the electrode device 16 are temperature sensors 40 for monitoring the temperature of the electrode device 16 at various points along its length. In one embodiment, each band electrode 32 has a temperature sensor 40 mounted to it. Each temperature sensor 40 provides a temperature signal 22 to the controller 20 which is indicative of the temperature of the respective band electrode 32 at that sensor. In another embodiment of the electrode device 16 a temperature sensor 40 is mounted on every other band electrode 32. Thus for a catheter having twelve electrodes, there are temperature sensors on six electrodes. In yet another embodiment of the electrode device 16 every other electrode has two temperature sensors 40. In FIG. 1, which shows an embodiment having one temperature sensor for each electrode, there is shown a single power lead 15 for each electrode 32 to provide power to each electrode for ablation purposes and two temperature leads 23 for each temperature sensor 40 to establish the thermocouple effect.

In another approach, the drive wire may comprise one of the thermocouple wires or may comprise a common wire for a plurality of thermocouples mounted on the same electrode. The inventor hereby incorporates by reference his pending application Ser. No. 09/072,800 entitled "Catheter Having Common Lead for Electrode and Sensor" May 5, 1998, and pending application Ser. No. 09/072,853 entitled "Electrode Having Non-Joined Thermocouple for Providing Multiple Temperature-Sensitive Junctions" May 5, 1998.

Turning now to FIGS. 2-1 and 2-2, a block diagram of an ablation apparatus 10 and method in accordance with aspects of the invention is presented. In FIGS. 2-1 and 2-2, a single channel of the power control system 12 is depicted. This channel controls the application of power to a single electrode 32. As will be discussed in relation to other figures, a channel may control a plurality or group of electrodes. In FIG. 2-1, a microprocessor 42, which is part of the controller 20 (FIG. 1), provides a duty cycle control signal 44 to a duty cycle generator 45. In this case, the duty cycle generator 45 ("DCG") 45 receives the control signal 44 by an 8-bit latch 46. The latch 46 provides an 8-bit signal 47 to a duty cycle comparator 48. The comparator 48 compares the 8-bit signal 47 to a count from an 8-bit duty cycle counter 50 and if the count is the same, provides a duty cycle off signal 49 to the duty cycle gate 52. The gate 52 is connected to a frequency source ("FS") 54, such as an oscillator that produces 500 kHz. When the gate 52 receives the duty cycle off signal 49 from the comparator 48, it stops its output of the frequency source signal through the gate and no output exists.

At a frequency of 500 kHz, an 8-bit control has a period or time frame of 0.5 msec. At a fifty-percent duty cycle, the electrode is in the off period only 0.25 msec. To allow for greater cooling of the electrode, the period or time frame 78 (FIG. 6) is lengthened by use of a prescalar 56 interposed between the frequency source 54 and the counter 50. In one embodiment, the prescalar 56 lengthens the period to 4 msec thus allowing for a 2 msec off period during a fifty-percent duty cycle. This results in a sufficient cooling time for the very thin band electrodes discussed above. Other lengths of the period may be used depending on the circumstances. It has been found that a ten percent duty cycle is particularly effective in ablating heart tissue. The combination of the application of high peak power, a ten percent duty cycle, the use of high thermal conductivity material in the band electrodes, and fluids flowing past the band electrodes which have a cooling effect on the electrodes result in a much more effective application of power to the tissue. Ablation occurs much more rapidly.

A terminal count detector 58 detects the last count of the period and sends a terminal count signal 59 to the gate 52 which resets the gate for continued output of the frequency source signal. This then begins the on period of the duty cycle and the counter 50 begins its count again. In one preferred embodiment, the duty cycle is set at fifty percent and the 8-bit latch is accordingly set to 128. In another embodiment, the duty cycle is set at ten percent.

A programmable logic array ("PLA") 60 receives phase control signals 61 from the microprocessor 42 and controls the phase of the frequency source 54 accordingly. In one embodiment, the PLA 60 receives the terminal count signal 59 from the terminal count detector 58 and only permits phase changes after receiving that terminal count signal.

The output signal from the gate 52 during the on period of the duty cycle is provided to a binary power amplifier ("BPA") 62 that increases the signal to a higher level, in this case, 24 volts. The amplified signals are then filtered with a band pass filter 64 to convert the somewhat square wave to a sine wave. The band pass filter ("BPF") 64 in one embodiment is centered at 500 kHz. The filtered signal is then provided to an isolated output ("IOT") transformer 66 that amplifies the signal to a much higher level, for example 350 volts peak-to-peak. This signal is then sent to a relay interconnect ("RI") 67 before it is provided as a power output signal OUTn 14 to an electrode 32 at the biological site to cause ablation.

The power output signal 14 from the isolated output transformer 66 is monitored in one embodiment to determine the impedance at the electrode 32. In the embodiment shown in FIGS. 2-1 and 2-2, a voltage and current monitor ("VCM") 68 is used. The monitor signal 69 is converted to digital form by an A-to-D converter ("ADC") 70 and provided to the microprocessor 42. As previously mentioned, some or all of the electrodes 32 may include a temperature sensor 40 (FIG. 1) that provides temperature signals 22 (FIG. 2-2) which are used to determine the temperature at the electrode 32. In one embodiment of the invention, the power 14, in conjunction with the temperature signals 22, are used to determine the temperature at the electrode 32. Both the temperature signals 22 and the power 14 pass through a temperature filter ("FL") 73 before being sent to the microprocessor 42. In the alternative, the temperature filter 73 is contained in a printed circuit board separate from the controller 20 and contains its own processor. In either case, the filter 73 filters out any RF noise present in the power 14 so that the signal may be used for temperature monitoring purposes. In another embodiment, the microprocessor monitors the power 14 and temperature signals 22 only during the off periods of the power 14 duty cycle. Accordingly, negligible RF noise is present in the power line and filtration is not necessary. In either embodiment, the microprocessor 42 may alter the duty cycle of the power 14 in response to either or both of the impedance or temperature signals.

In a manual arrangement, the temperature sensed and/or the determined impedance may be displayed to an operator.

The operator in response may then manually control the duty cycle or other power parameters such as by rotating a knob mounted on a front panel of an instrument. In the case of a multiple channel instrument and catheter, as discussed below, multiple knobs may be provided in this manual arrangement for control over each channel.

Figure 3:
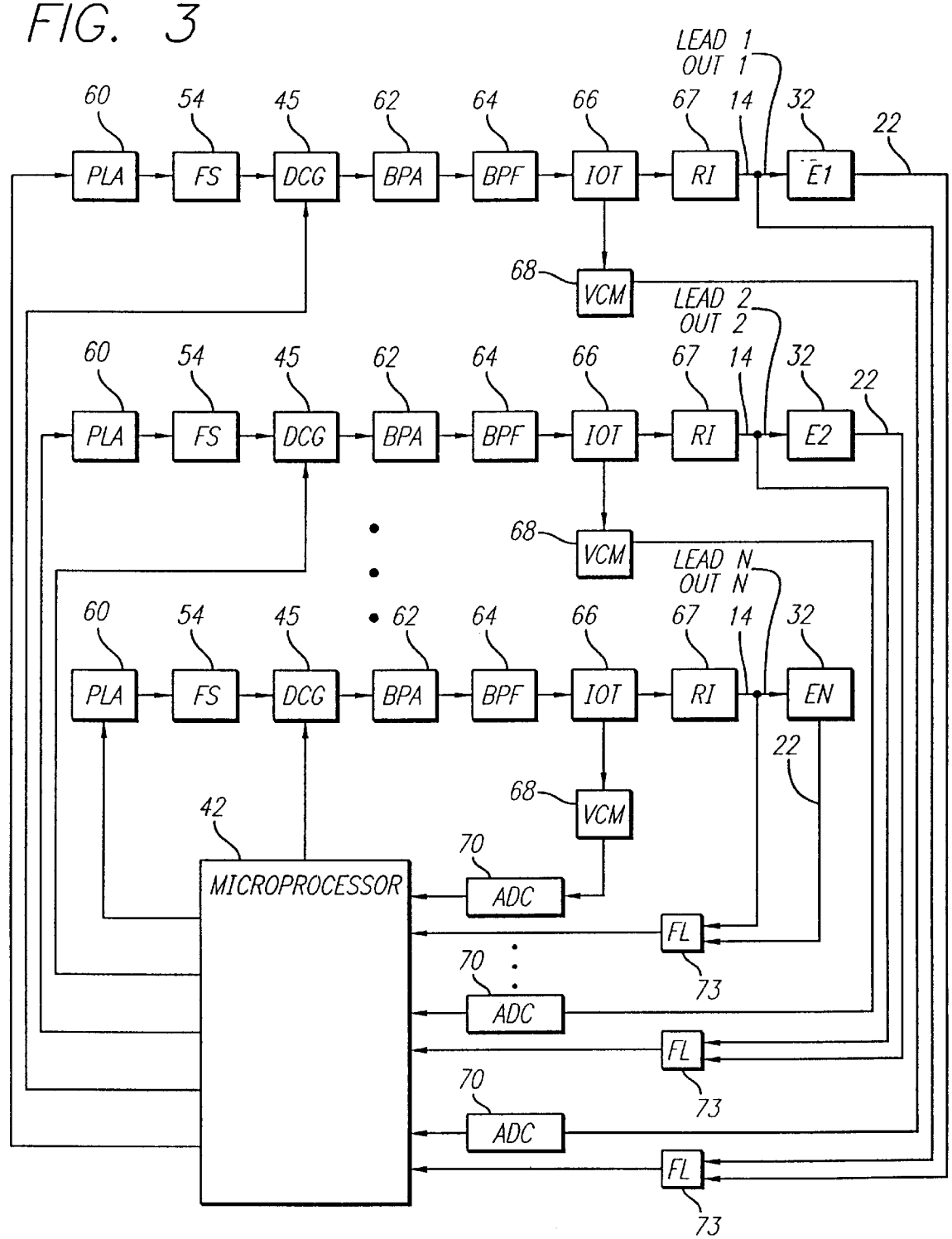
FIG. 3 is a diagram of a multi-channel ablation apparatus in accordance with aspects of the invention wherein a single microprocessor controls the phase angle and duty cycle of each channel individually.

Referring now to FIG. 3, a multiple channel ablation apparatus is shown. Although only three complete channels are shown, the apparatus comprises many more as indicated by the successive dots. Those channels are not shown in FIG. 3 to preserve clarity of illustration. By providing different voltage levels between two electrodes 32 in an array, current flows between those electrodes in a bipolar electrode approach. By setting the backplate 24 (FIG. 1) at a voltage level different from at least one of those electrodes 32, current flows between that electrode and the backplate. By controlling the voltage levels among the three (two electrodes and backplate), the current flow through the biological site 26 can be more precisely controlled. One technique for setting different voltage levels between the electrodes 32 is to maintain a phase difference between them in an AC approach. By setting the backplate 24 at the reference level, current flows between the electrodes 32 and the backplate.

The single microprocessor 42, which again is part of the controller 20 (FIG. 1), controls the duty cycle and the phase of each channel individually in this embodiment. Each channel shown comprises the same elements and each channel produces its own power output signal 14 (OUT1, OUT2, through OUTn where "n" is the total number of channels) on respective electrode leads (LEAD 1, LEAD 2, through LEAD n where "n" is the total number of leads) to the electrodes 32. This multi-channel approach permits more individual control over each electrode. For example, the duty cycle of the power applied to each electrode can be individually controlled. One electrode may have a ten percent duty cycle while another has a thirty percent duty cycle.

Referring now to the first and second output signals OUT1 and OUT2 of FIG. 3, the signals, as shown in FIGS. 4, 5, and 6, have alternating instances of peak power i. e., "on" periods 74, and very low power 76, i.e., "off" periods. Typically, the output power 14 is a 500 kHz sine wave. In FIGS. 4 and 5, number of cycles of the sine wave contained within one on period 74 has been substantially reduced in the drawing to emphasize the phase difference between the first and second output signals OUT1, OUT2. Preferably, the voltage of each power signal 14 during an off period 76 is substantially zero and during an on period 74 is approximately 350 volts peak-to-peak.

The power OUT1 and OUT2 also have a variable duty cycle for controlling the length of the on period 74 and the off-period 76 within a time frame 78 (see FIG. 6). The duty cycle is the ratio of the length of the on period 74 to the length of the entire time frame 78. The effective power is the peak power times the duty cycle. Thus, a signal having a peak power of 100 watts and a 50% duty cycle has an effective power of 50 watts.

Figure 7B:
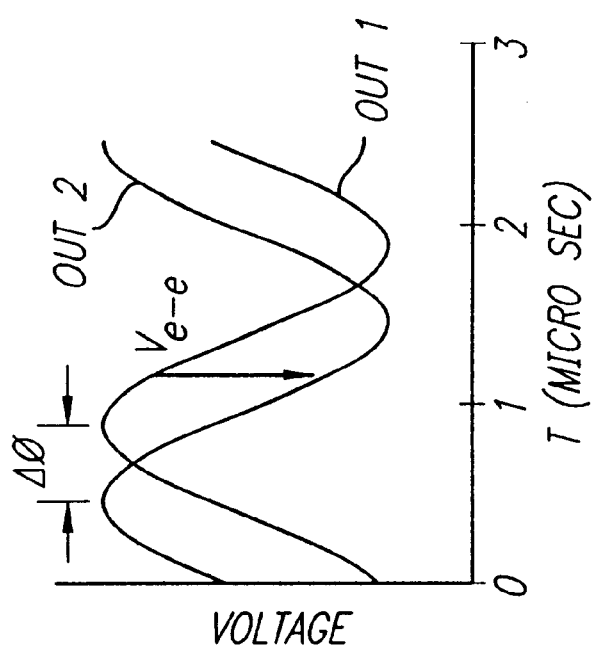
FIG. 7B depicts the phase relationship and voltage potential between the first and second power waveforms having second and first phase angles respectively, as a function of time.
Figure 7A:
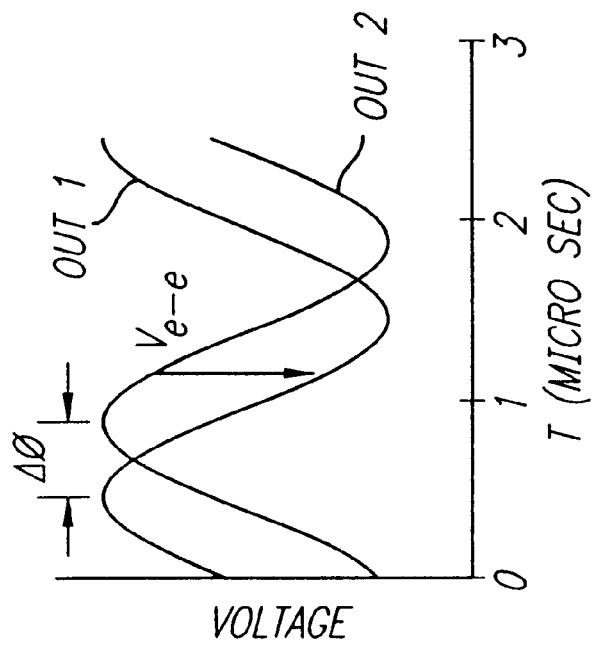
FIG. 7A depicts the phase relationship and voltage potential between the first and second power waveforms having first and second phase angles respectively, as a function of time.

As shown in FIGS. 4, 5, and 6, the two power signals OUT1, OUT2 are phased differently from each other. As discussed above, the phase angle of each power signal is set and controlled by the processor 42 and PLA 60. Each power signal OUT1 and OUT2 has a respective phase angle and those phase angles differ between the two of them. The phase angle difference between the power OUT1 and OUT2 produces a voltage potential between the band electrodes 32 (FIG. 1) that receive the power. This voltage potential, in turn, induces current flow between the band electrodes 32. The phase angle relationship of the power and the voltage potential produced as a function of time is shown in FIGS. 7A and 7B. The potential between electrodes $V_{e-e}$ is defined by:

$$V_{e-e} = 2V \sin\left(\frac{\Delta\Phi}{2}\right)\sin(2\pi ft) \quad \text{(Eq. 1)}$$

FIG. 7A shows first and second power OUT1 and OUT2 provided to first and second electrodes respectively having a phase angle difference $\Delta\Phi$ with OUT1 leading OUT2 by 132 degrees. FIG. 7B shows the same power OUT1 and OUT2 but with the phase angles reversed where OUT2 is now leading OUT1 by 132 degrees.

Figure 8C:
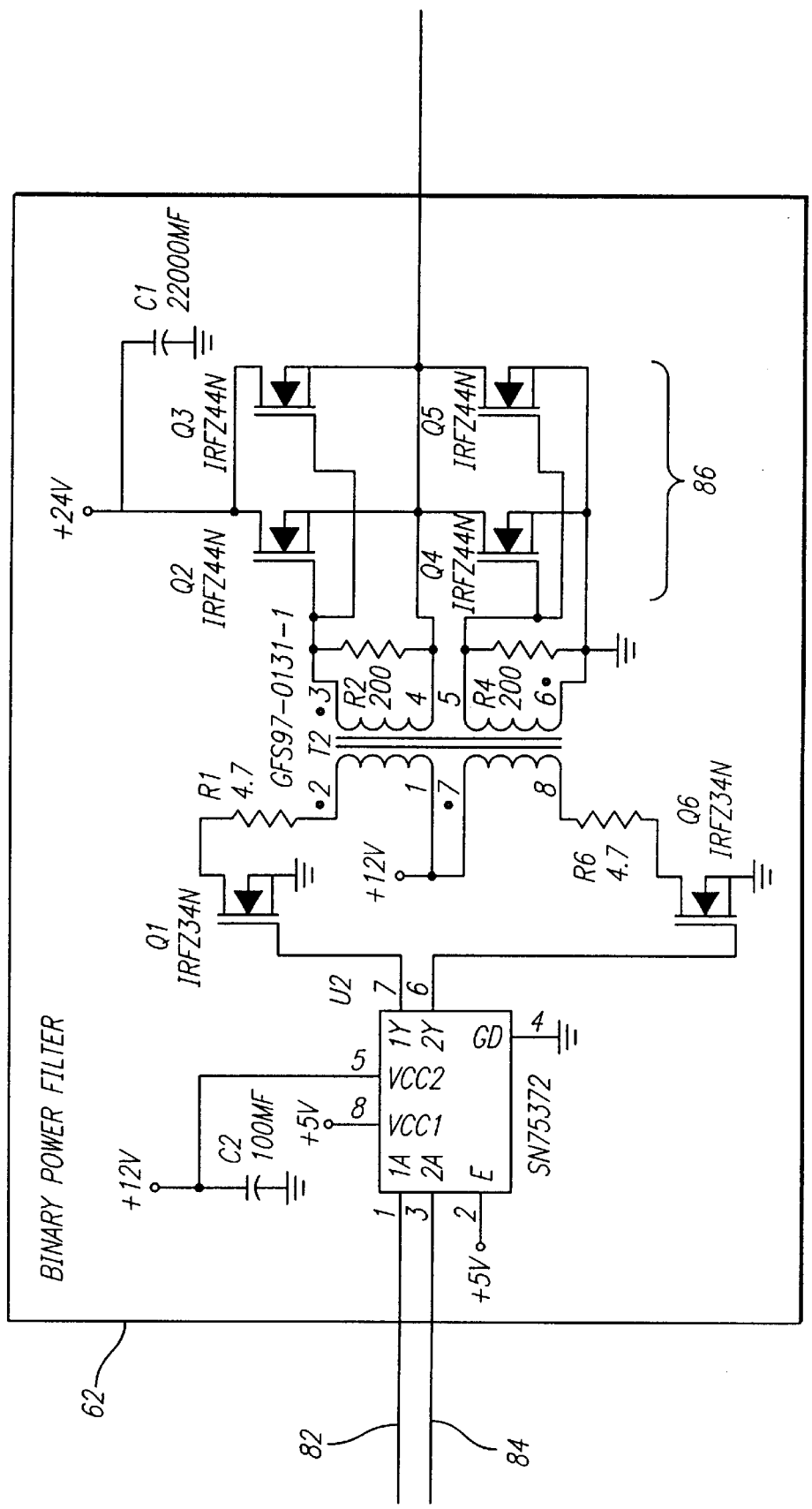
Figure 8D:
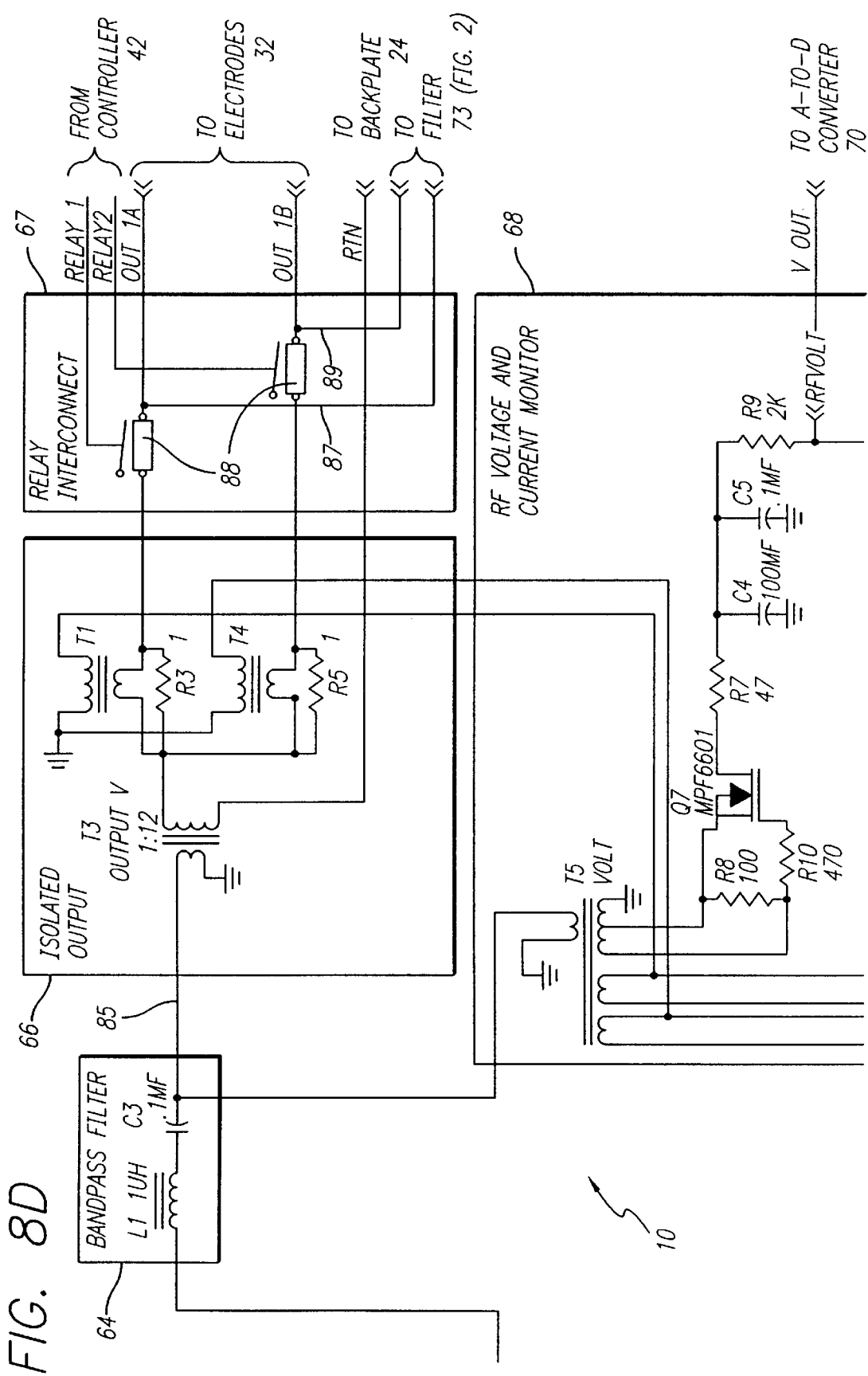
Figure 8E:
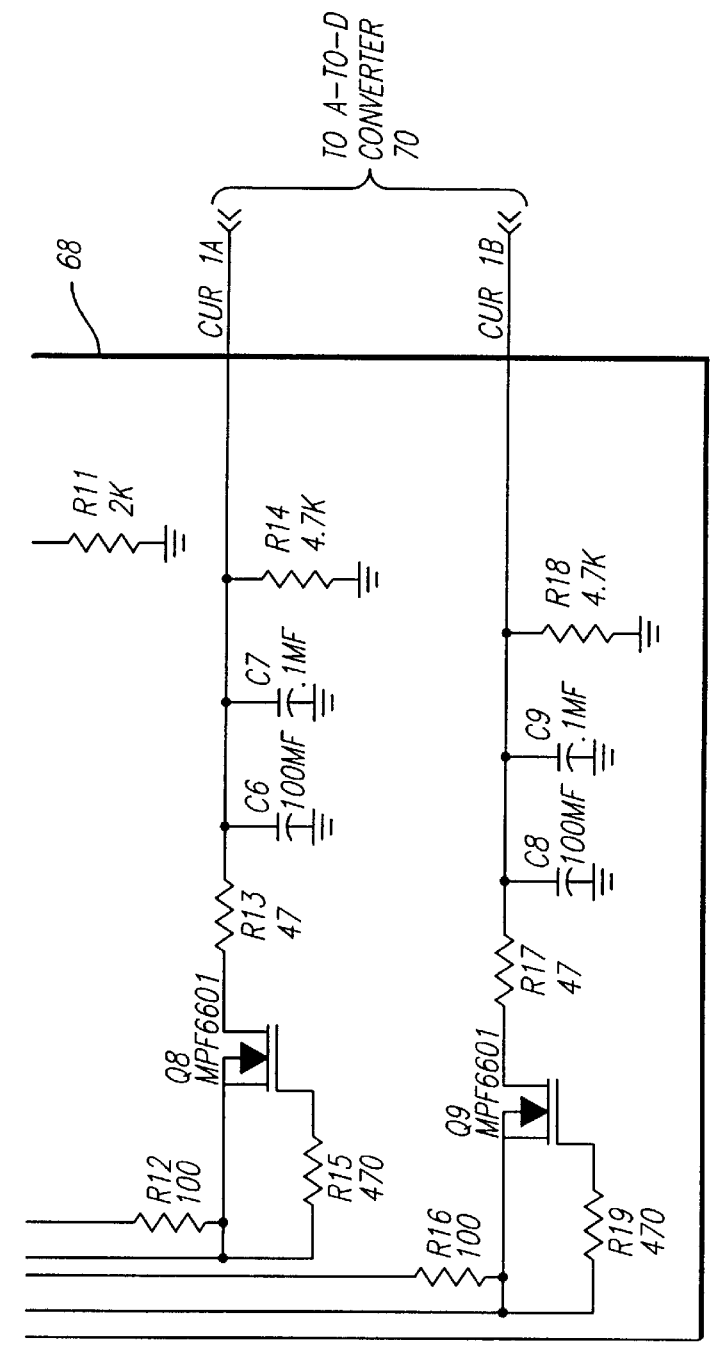
Figure 9A:
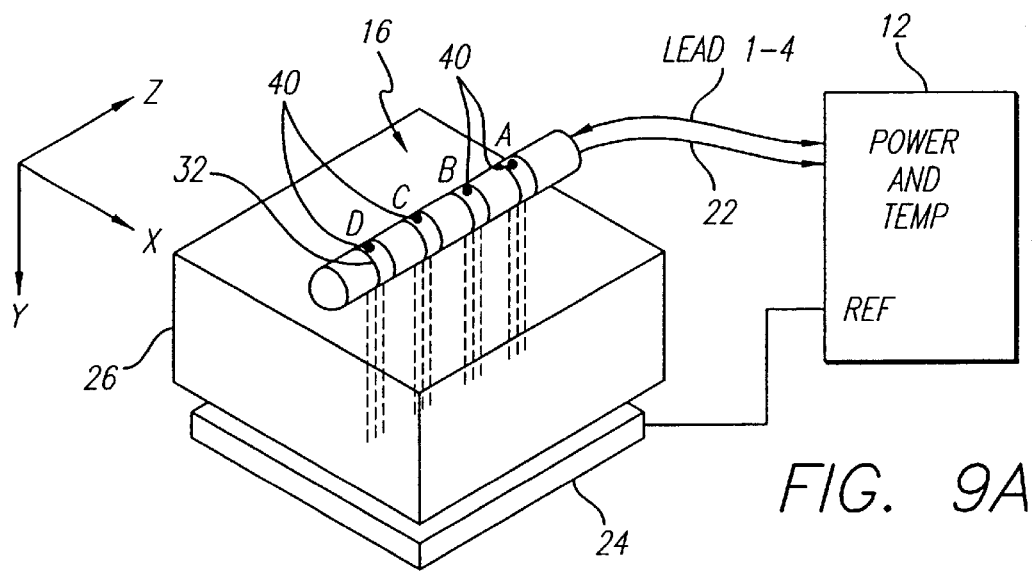
FIG. 9A is a three dimensional representation of an ablation apparatus having a linear array of band electrodes in contact with a biological site with a backplate at the opposite side of the biological site, in which the phase angle difference between adjacent electrodes of the linear array is zero degrees.
Figure 9B:
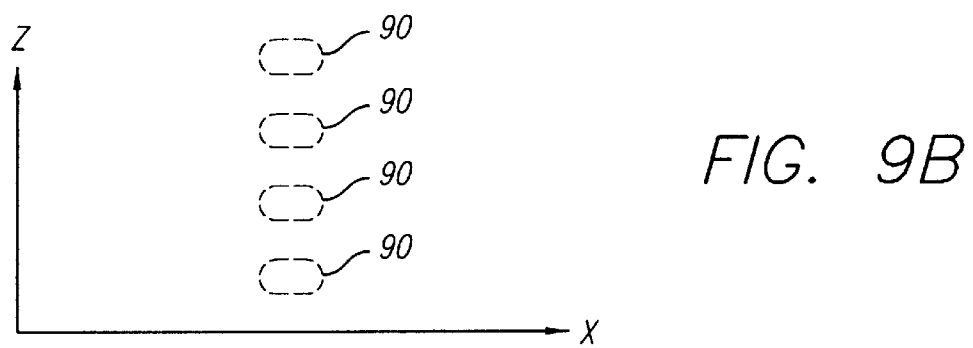
FIGS. 9B through 9D depict, along the x, y, and z axes shown, the depth of the lesions formed by the ablation apparatus of FIG. 9A showing that the apparatus acts as a unipolar device with multiple electrodes and the resulting lesions are discontinuous.
Figure 9C:
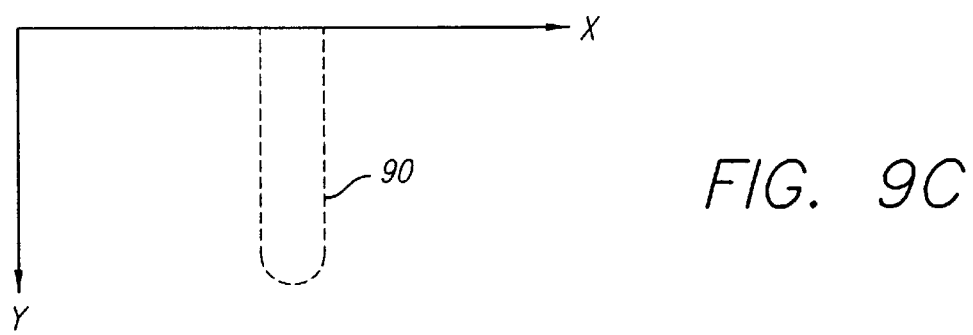
Figure 9D:
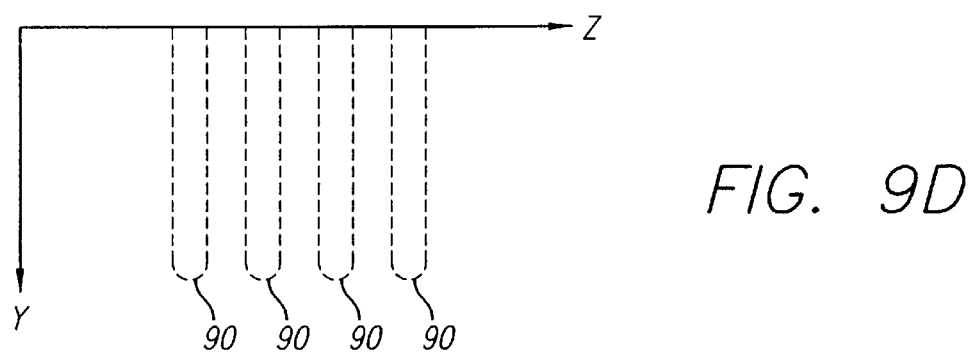

With reference now to FIGS. 8 through 8E, schematic diagrams of an embodiment of the ablation apparatus 10 of FIGS. 2-1 and 2-2 are presented in FIGS. 8B through 8E while FIG. 8A shows how FIGS. 8B through 8E should be oriented in relation to each other. The frequency source 54 provides a signal 80, typically at 500 kHz with a phase angle controlled by the microprocessor 42 through the PLA 60, to the duty cycle generator 45. The duty cycle generator 45 modulates the frequency source signal 80 to produce the selected duty cycle in accordance with the duty cycle control signal 44 as previously described. The duty cycle generator 45 outputs two signals 82 and 84 to the binary power amplifier 62. A dual MOSFET driver U2 receives the signals, converts their 5V level to a 12V level, and sends each to a transformer T2 which transforms the signals into 24 V peak-to-peak power.

The 24V power is then sent to a multi-state driver 86 which includes a configuration of FETs Q2, Q3, Q4, and Q5. During a conducting state of the driver 86, which is typically the on period 74 of the power, these FETs Q2 through Q5 conduct and forward the power to a bandpass filter 64 comprising a series LC network. During a high-impedance state of the driver 86, which is typically during the off period 76 of the power, the FETs Q2 through Q5 are nonconducting and no power is sent to the bandpass filter 64. Instead the FETs Q2 through Q5 present a high impedance load to any signals received through the electrode 32. Typically the load impedance on the FETs Q2 through Q5 presented by the circuit following the FETs, the electrode, and the tissue is approximately 150Ω but transformed through the output transformer T3, it presents a load impedance to the FETs Q2–Q5 of approximately 0.5 to 1Ω. In the off state, the FETs present an impedance of approximately 250Ω which is large in comparison to the transformed load impedance of approximately 0.5 to 1Ω. Therefore, very little power flows when the FETs are in the off state.

The bandpass filter 64 operates to shape the output signal provided by the binary amplifier 62 from a square wave to a sinusoidal wave. The filtered signal 85 then passes to the isolated output section 66 where it is step-up transformed to 350 volt peak-to-peak sinusoidal power at T3. The power is then split into two identical power signals OUT1A, OUT1B and provided to two or more respective band electrodes 32 on the output lines LEAD1A, LEAD1B.

The isolated output section 66 also includes relays 88 that may be individually opened to remove the power signals OUT1A, OUT1B from the electrode leads LEAD 1A, LEAD 1B when an alert condition is detected, such as high temperature or high impedance at the respective electrode 32. As previously mentioned these conditions are determined by the microprocessor 42 which receives signals indicative of the temperature and impedance at each of the band electrodes 32.

The power from the isolated output section 66 is monitored and representative signals are supplied to an RF voltage and current monitor 68 where in this case, the voltage and current of each output signal are measured to determine the impedance of the particular channel. The measured signals are sent to an A-to-D converter 70 (FIG. 2-2) before being sent to the microprocessor 42 for impedance monitoring. If the impedance is above a threshold level indicative of blood clotting or boiling, the microprocessor 42 sends a signal to the duty cycle generator 45 to reduce or discontinue the duty cycle of the power OUT1A, OUT1B and thus lower the effective power delivered to the band electrodes 32.

Similarly, the temperature at the electrodes 32 is determined by monitoring the power 14 and temperature signals 22 and measuring the voltage difference between the signals. As previously mentioned, in one embodiment of the invention, these signals pass through a filter 73 (FIG. 2-2) before being sent to the microprocessor 42. The voltage value is converted to a temperature and if the temperature is above a threshold level the duty cycle of the power 14 is reduced. In the case where a single lead is used to provide a signal which is used to determine the temperature as well as provide power to the electrode 32, the signal from the lead is received on temperature leads 87, 89 connected at the output side of the relays 88.

As shown in FIG. 3, the duty cycle of each electrode 32 may be individually controlled by the microprocessor 42. As previously mentioned, based on the temperature at an electrode 32 and the current and voltage of the output signal provided to an electrode, the duty cycle of the output signal may be adjusted. For example, one electrode 32 may have a temperature requiring a duty cycle of ten percent, while another electrode may have a temperature which allows for a fifty percent duty cycle. In an embodiment in which every other electrode 32 has a temperature sensor 40, the electrodes are grouped in pairs with each electrode in the pair having the same duty cycle.

In operation, as depicted in FIGS. 9A through 11D, the electrode device 16 and the backplate 24 are positioned proximal the biological site 26 undergoing ablation such that the biological site is interposed between the electrode device and the backplate. The band electrodes 32 (only one of which is indicated by a numeral 32 for clarity of illustration) of the electrode device 16 each receives power OUT1, OUT2, OUT3, OUT4 having a phase angle on LEAD 1 through LEAD 4. In one embodiment, every other electrode 32 receives the same phase angle. Therefore, the phase angle of electrode A equals the phase angle of electrode C and the phase angle of electrode B equals the phase angle of electrode D. The advantages of this arrangement are described below. In a preferred embodiment, the electrodes 32 are formed into a linear array as shown. In addition, a thermocouple temperature sensor 40 is located at each of the electrodes A, B, C, and D and uses the electrode power lead LEADS 1 through 4 as one of the sensor leads. The sensors 40 provide temperature sensor signals 22 for receipt by the power control system 12.

In another embodiment, alternate electrodes 32 may be grouped together and each may receive the same power having the same phase angle and duty cycle. Another group or groups of electrodes 32 may be interspaced with the first group such that the electrodes of one group alternate with the electrodes of the other group or groups. Each electrode 32 in a particular group of electrodes has the same phase angle and duty cycle. For example, electrodes A and C may be connected to the same power while interspaced electrodes B and D may be connected to a different power output signal.

The use of individual power signals also provides the ability to disable any combination of electrodes 32 and thereby effectively change the length of the electrode device 16. For example, in one configuration of the present invention an electrode device 16 with twelve electrodes 32 receives twelve power signals from a twelve channel power control system 12. The electrodes 32 are 3 mm in length and are 4 mm apart. Accordingly, by disabling various electrodes, a virtual electrode of any length from 3 mm to 8 cm may be produced by the electrode device 16. In either arrangement the backplate 24 is maintained at the reference voltage level in regard to the voltage level of the power OUT1 through OUTn.

As previously described, by varying the phase angles between the power OUT1, OUT2 supplied to each electrode 32, a phase angle difference is established between adjacent band electrodes. This phase angle difference may be adjusted to control the voltage potential between adjacent band electrodes 32 and thus to control the flow of current through the biological site 26. The flow of current $I_{e-e}$ between adjacent band electrodes 32 is defined by:

$$I_{e-e} = \frac{2V \sin\left(\frac{\Delta\Phi}{2}\right)\sin(2\pi ft)}{Z_{e-e}} \quad \text{(Eq. 2)}$$

In addition to the current flow between the band electrodes 32 there is current flow between the band electrodes and the backplate 24. When the backplate 24 is set at the reference level, this current flow $I_{e-b}$ is defined by:

$$I_{e-b} = \frac{V \sin(2\pi ft)}{Z_{e-b}} \quad \text{(Eq. 3)}$$

Assuming $Z_{e-b}$ and $Z_{e-e}$ are equal, the ratio of the current flowing between the band electrodes 32 $I_{e-e}$ to the current flowing between the band electrodes 32 and the backplate 24 $I_{e-b}$ is defined by:

$$\frac{I_{e-e}}{I_{e-b}} = 2\sin\left(\frac{\Delta\Phi}{2}\right) \quad \text{(Eq. 4)}$$

where:

$\Delta\Phi$=phase angle difference between electrodes

FIGS. 9 through 11 illustrate various current flow patterns within a biological site. The depths and widths of the lesions depicted in FIGS. 9A through 11D are not necessarily to scale or in scalar proportion to each other but are provided for clarity in discerning the differences between the various power application techniques. When the phase difference between adjacent electrodes 32 is zero degrees, no current flows between the electrodes in accordance with Eq. 2 above, and the apparatus operates in a unipolar fashion with the current flowing to the backplate 24 as shown in FIGS. 9A through 9D. Substantially all current flows from the band electrodes 32 to the backplate 24 forming a series of relatively deep, acute lesions 90 along the length of the electrode device 16. As seen in the top view of FIG. 9B and the side view of FIG. 9D, the lesions are discrete. The lesions 90 are discontinuous in regard to each other.

Figure 10A:
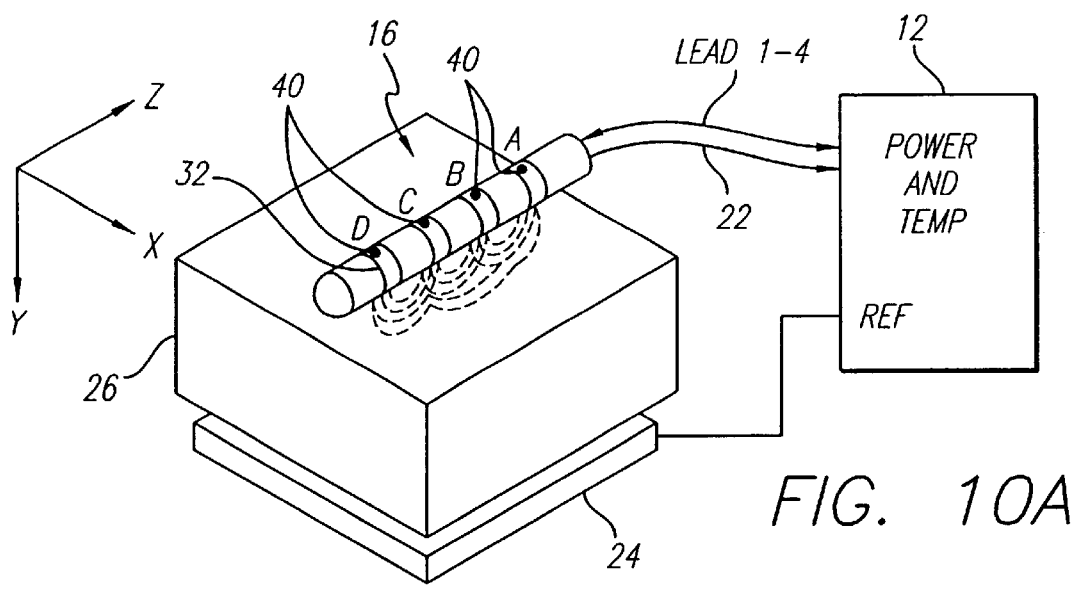
FIG. 10A is a three dimensional representation of an ablation apparatus having a linear array of band electrodes in contact with a biological site with a backplate at the opposite side of the biological site, in which the phase angle difference between adjacent electrodes is 180 degrees.
Figure 10B:
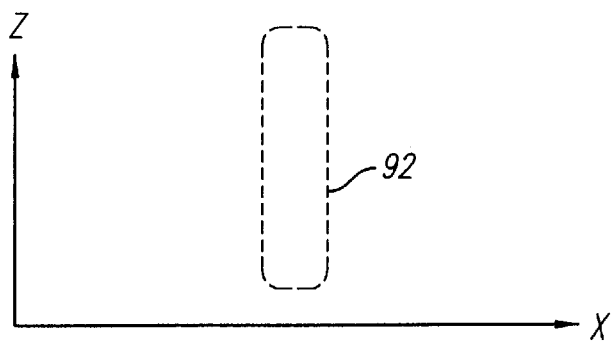
FIGS. 10B through 10D depict, along the x, y, and z axes shown, the continuity and depth of a lesion formed by the ablation apparatus of FIG. 10A showing that the apparatus acts as a bipolar device with no significant amount of current flowing to the backplate.
Figure 10C:
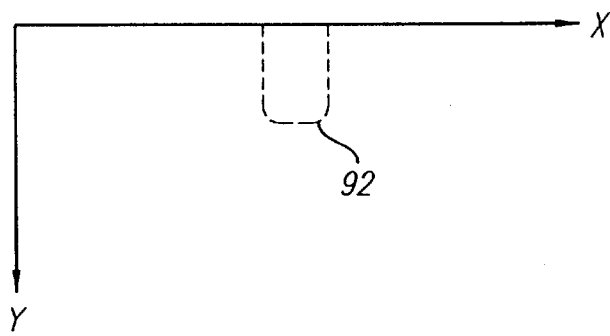
Figure 10D:
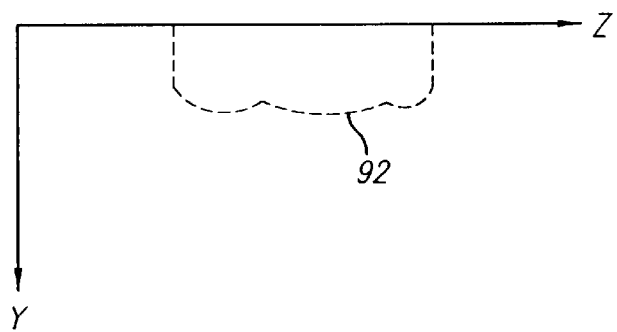

When the phase difference between adjacent electrodes 32 is 180 degrees the apparatus operates in both a unipolar and bipolar fashion and the current flow pattern is as shown in FIG. 10A. With this phase difference, approximately twice as much current flows between adjacent band electrodes 32 than flows from the band electrodes to the backplate 24. The resulting lesion 92 is shallow but is continuous along the length of the electrode device 16. The continuity and shallow depth of the lesion 92 are illustrated in FIGS. 10B through 10D. Nevertheless, the lesion depth is still greater than that created by prior bipolar ablation methods alone.

Figure 11A:
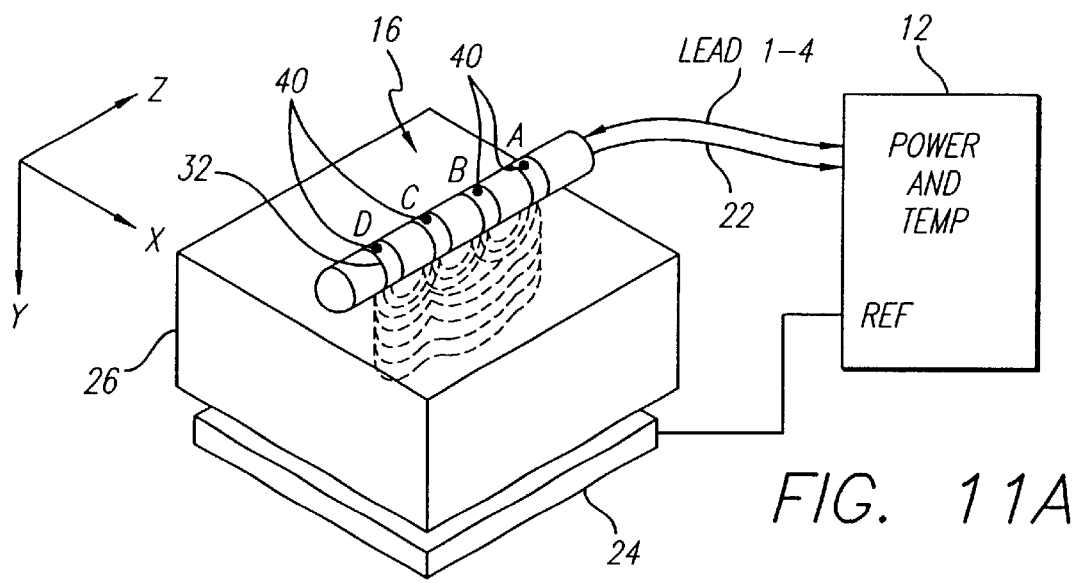
FIG. 11A is a three dimensional representation of an ablation apparatus having a linear array of band electrodes in contact with a biological site with a backplate at the opposite side of the biological site, in which the phase difference between adjacent electrodes is approximately 90 degrees.
Figure 11B:
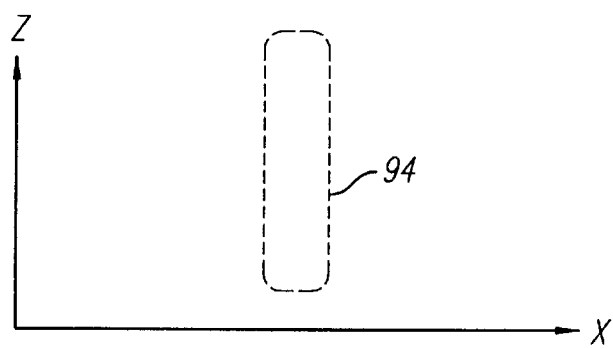
FIGS. 11B through 11D depict, along the x, y, and z axes shown, the continuity and depth of a lesion formed by the ablation apparatus of FIG. 11A showing the greater depth of lesion resulting from the phase angle difference.
Figure 11C:
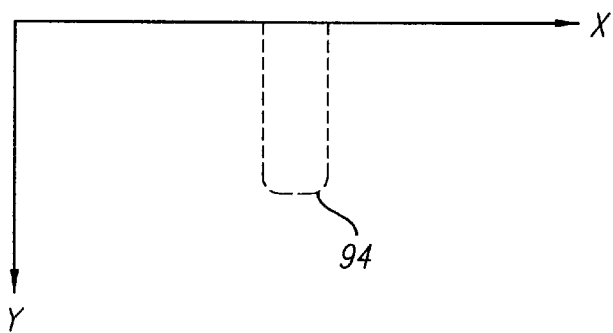
Figure 11D:
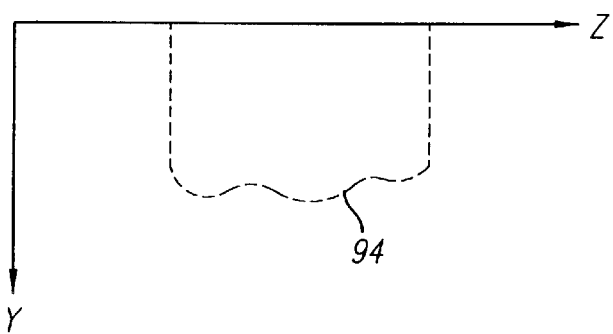

When the phase difference between adjacent electrodes 32 is set within the range of a value greater than zero to less than 180 degrees, the current flow varies from a deep, discontinuous unipolar pattern to a more continuous, shallow bipolar pattern. For example, when the phase difference between adjacent electrodes 32 is around 90 degrees, the current flows as shown in FIG. 11A. With this phase difference, current flows between adjacent band electrodes 32 as well as between the band electrodes and the backplate 24. Accordingly, a lesion which is both deep and continuous along the length of the electrode device 16 is produced. The continuity and depth of the lesion 94 is illustrated in FIGS. 11B through 11D. In one embodiment of FIG. 11A, adjacent electrodes alternated in phase but were provided with power in groups. Electrodes A and C were provided with power at a first phase angle and electrodes B and D were provided with power at a second phase angle, different from the first.

Thus, the phase angle of the power may be adjusted in order to produce a lesion having different depth and continuity characteristics. In selecting the phase angle difference necessary to produce a continuous lesion having the greatest possible depth, other elements of the electrode device 16 are considered. For example, the width of the band electrodes 32 and the spacing between the electrodes are factors in selecting an optimum phase angle. In a preferred embodiment of the present invention, as pointed out above, the width of the band electrodes is 3 mm, the spacing between the electrodes is 4 mm and the electrodes receive power which establish a phase difference of 132 degrees between adjacent electrodes. With this configuration a long continuous lesion having a length of between approximately 3 mm and 8 cm and a depth of 5 mm or greater was produced depending on the number of electrodes energized, the duty cycle employed, and the duration of power application.

In another embodiment, energy is applied to the biological tissue 26 during the on period of the duty cycle in an alternating unipolar-bipolar manner. During the unipolar mode segment a voltage potential is established between the electrodes 32 and the backplate 24. Thus current flows through the tissue 26 between the electrodes 32 and the backplate 24.

During the bipolar mode segment a voltage potential is established between at least two of the electrodes 32 rather than between the electrodes and the backplate 24. Thus current flows through the tissue 26 between the electrodes 32. While operating in this mode the voltage difference between the electrodes 32 may be established by providing power with different phase angles to the electrodes as previously mentioned. Alternatively, some of the electrodes 32 may be connected to a reference potential while others are maintained at a different voltage level.

By adjusting the duration of the unipolar and bipolar mode segments within the on period of the duty cycle, the continuity and depth of the lesion produced may be controlled. For example, operating in the unipolar mode for one-fourth of the on period and in the bipolar mode for three-fourths of the on period produces a lesion having a continuity and depth similar to the lesion 94 illustrated in FIGS. 11B through 11D.

Referring to FIGS. 8B through and 8E, the following devices are shown:

| Device | Part No. | Manufacturer |
| --- | --- | --- |
| U1 | GAL6002B | Lattice |
| U2 | SN75372 | numerous |
| Q1 | 1RFZ34N | numerous |
| Q2, Q3, Q4, Q5 | 1RFZ44N | numerous |
| Q7, Q8, Q9 | MPF6601 | numerous |
| R3, R5 | 1Ω | numerous |
| T1, T4 | CMI-4810 | Corona Magnetics, Inc. |
| T2 | GFS97-0131-1 | GFS Manufacturing |
| T5 | CMI-4809 | Corona Magnetics, Inc. |

The transformer denoted by "T3" is a 1:12 turns ratio, single turn primary, step up transformer wound on a TDK core PC50EER23Z.

The band electrodes 32 generate a heating pattern in the tissue by transmitting RF power into the tissue. The power supplied to the band electrodes 32 is typically increased in order to increase the ablation volume until either an impedance change is noticed due to the onset of clotting or the temperature limit set for the electrode is reached. When one or both of these conditions exist the effective power delivered to the band electrodes 32 is reduced by reducing the duty cycle of the power signal in this embodiment.

The band electrodes 32 are designed to heat a volume of tissue to an ablation temperature while at the same time assuring that the peak temperature of the band electrodes is controlled so that clotting does not foul the electrode surface and blood boiling does not occur. To this end, each of the band electrodes 32 is formed from a biocompatible material having a high thermal conductivity. It is preferred that the materials exhibit substantially the same thermal and electrical conductivity properties. The following metals are provided for example in descending order of electrical conductivity as measured using the International Annealed Copper Standard (IACS): silver, gold, chromium, aluminum, molybdenum, tungsten, nickel, platinum, and platinum/10% iridium.

In one embodiment, that material is substantially pure platinum. Pure platinum is preferred over platinum/10% iridium, which is commonly used in electrophysiology catheters, because it has been found to produce larger lesions with lesser incidence of impedance rise at the electrode/tissue interface. Pure platinum also has a more reliable thermoelectric performance. In order to retain substantially the same thermal conductivity that pure platinum has in its raw form and to provide an electrode 32 having a tensile strength greater than pure platinum in its raw form, the electrodes are formed using a cold work process as is well known to those skilled in the art of materials processing. The raw platinum is cold worked to a hardness greater than that which would be achieved by an annealing process and is preferably at least 50% cold worked.

To further assure that the peak temperature of the band electrodes is controlled, the band electrodes 32 are sized so that a large surface area is available for contact with the fluid in the heart for dissipating heat to the fluid around the electrode and thereby cooling the electrode. Also, the thickness of the band electrodes 32 is selected so that the electrodes effectively draw heat energy away from the target tissue for cooling purposes without unduly increasing the outside diameter of the electrode device.

Figure 13:
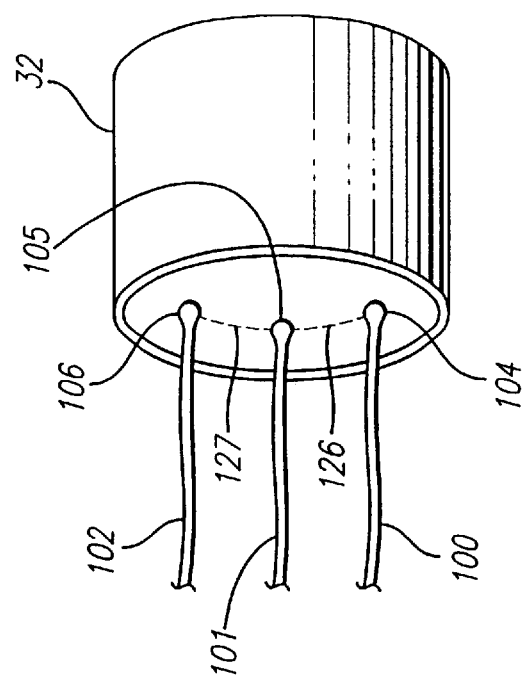
FIG. 13 is a diagram of a single band electrode showing the connection of two sensor thermocouple wires and a composition-matched, common-lead thermocouple wire.
Figure 12:
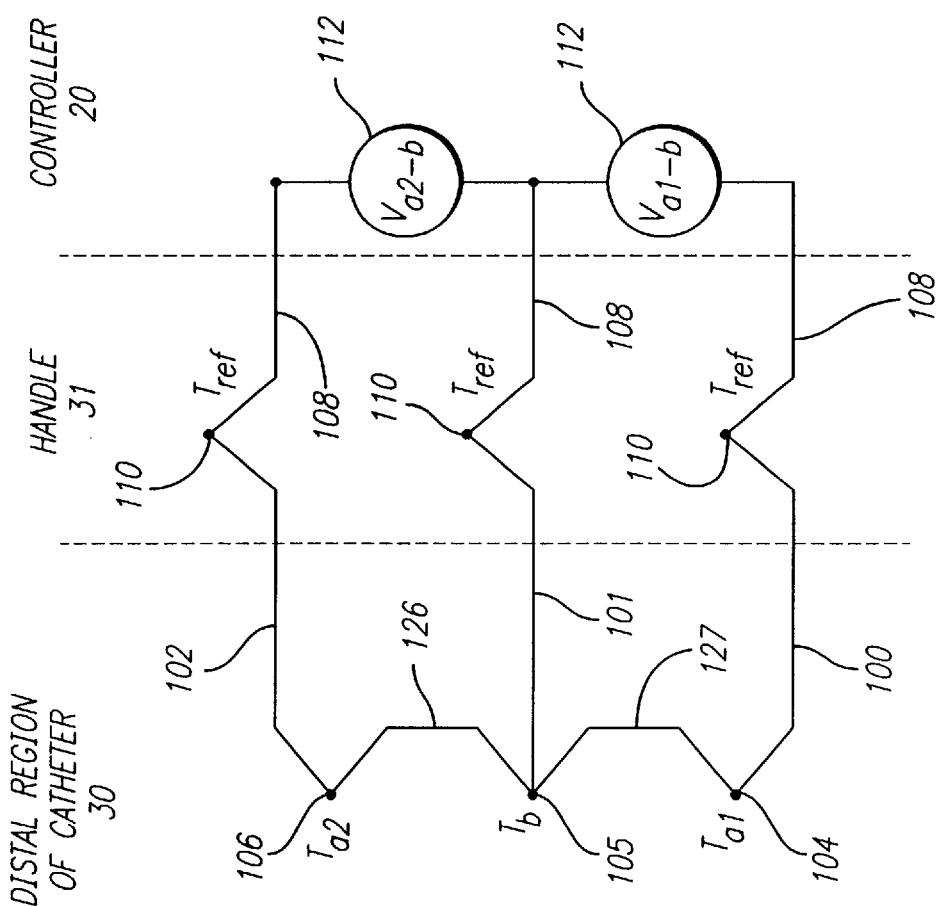
FIG. 12 is a schematic diagram of a thermocouple system having two sensor thermocouple wires and a composition-matched, common-lead thermocouple wire attached to a wire simulating a portion of a band electrode.

In accordance with aspects of the present invention, and with reference to FIGS. 12 and 13, first electrically conductive sensor lead 100, second electrically conductive sensor lead 102, and electrically conductive common lead 101 are connected independently to the band electrode 32 at two sensor junctions 104 and 106, and a common junction 105 respectively. Each of these junctions are separate from each other. These three electrically conductive members 100, 101, and 102 form the leads, i.e., or "legs" of what is essentially two thermocouples. Because of the separation between the locations at which the leads are attached to the inside surface of the band electrode, the portions 126 and 127 of the band electrode 32 between the connection points 104, 105, and 106 become part of the thermocouples and, in effect, serve as a large thermocouple bead. Associated with two of the junctions 104, 106 is a temperature-dependent voltage. This voltage is produced by the interface between two dissimilar metals and fluctuates in accordance with the temperature of the junction.

A conductive lead 108 is electrically connected to each sensor lead 100, 102 and the common lead 101 at a reference junction 110. A voltmeter 112 is disposed across the conductive lead 108 connected to first sensor lead 100 and the conductive lead 108 connected to the common lead 101 to measure the temperature-dependent voltage developed in the thermocouple formed by sensor lead 100, common lead 101, and thermocouple bead 127. Similarly, a voltmeter 112 is disposed across the conductive lead 108 connected to second sensor lead 102 and the conductive lead 108 connected to the common lead 101 to measure the temperature-dependent voltage developed in the thermocouple formed by sensor lead 102, common lead 101, and thermocouple bead 126. In order to correct for extraneous voltage due to dissimilar metal junctions at the voltmeter terminals, the reference-junction lead 108 is preferably made of the same material as the first and second sensor leads 100 and 102. The reference junction 110 and the leads for use in connection to the voltmeter are located in the handle 31 of the catheter and are therefore outside the patient. In another embodiment, the reference junctions 110 and conductive leads 108 are omitted and, as explained below, the reference temperature is assumed to be room temperature.

While FIGS. 12 and 13 depict only two sensor leads 100 and 102 it is possible to include a larger number of sensor leads positioned around the circumference of the band electrode 32. Each such sensor lead would form, in combination with the single common lead 101 and the thermocouple bead formed by the portion of the band electrode 32 between the sensor lead and common lead, a separate thermocouple. Each of these thermocouples provide a temperature-dependent voltage indicative of the temperature at the junction where the sensor lead is connected to the band electrode 32.

Conductive leads 100, 102, 108 are connected to a voltmeter 112 located within the controller 20 (FIG. 1). The voltmeter 112 (FIG. 12) provides voltage readings which are related to the temperatures at the various junctions 104, 106, and 110. The resulting voltage output $V_{ab}$ measured by each voltmeter 112 is expressed by the following general equation:

$$V_{ab}=\alpha_{ac}(T_a-T_{ref})-\alpha_{bc}(T_b-T_{ref}) \quad (Eq. 5)$$

$$V_{ab} = \alpha_{ac}(T_a - T_{ref}) - \alpha_{bc}(T_b - T_{ref}) \quad (Eq. 5)$$

$T_{ref}$ and the two Seebeck coefficients, $\alpha_{ac}$ and $\alpha_{bc}$, are typically known for the system at hand. As mentioned briefly above, the reference junction 110 is a controlled temperature junction which is normally included in order to correct for extraneous voltages due to dissimilar metal junctions at the voltmeter terminals. By being located in the handle, for example, the temperature is known to be room temperature, or approximately 22 degrees C. (72 degrees F.). In addition, the Seebeck coefficients are assumed to be constant over the range of temperatures typically encountered in cardiac ablation.

In accordance with the present invention, the material of the common lead 101 is chosen such that the temperature-dependent voltage produced at the common junction 105 is substantially zero. This is preferably done by forming the common lead 101 of the same material as the band electrode 32 or alternatively by forming the common lead of a material having a thermoelectric output very similar to that of the band-electrode material. Thus the electrode 32 is described as having a "composition-matched" common lead 101. In one embodiment of the invention the band electrode 32 and the common lead 101 are formed of substantially pure platinum. In another embodiment, the band electrode 32 is formed of substantially pure platinum and the common lead is formed of a copper/nickel alloy containing approximately 1–2% nickel, which is known to those skilled in the art as "alloy 11." In addition to its platinum like thermoelectric properties, alloy 11 is also preferred because it is a low cost alternative to pure platinum leads. In either embodiment, $\alpha_{bc}$ approximately equals zero and Eq. 5 reduces to:

$$V_{ab}=\alpha_{ac}(T_a-T_{ref}) \quad (Eq. 6)$$

The materials of the first and second sensor leads 100, 102 are chosen such that the magnitude of the Seebeck coefficients of the materials relative to the band electrode 32 material is large. In order to increase the voltage output and improve temperature measurement resolution, preferably, the material of the first and second sensor leads 100, 102 is chosen such that the ratio of the magnitude of the Seebeck coefficient of the sensor lead 100, 102 material relative to the band electrode 32 material and the magnitude of the Seebeck coefficient of the common lead 101 material relative to the band electrode 32 is at least ten to one. In one preferred embodiment, the first and second sensor leads 100 and 102 were formed of constantan. Constantan is preferred because it has a large Seebeck coefficient relative to platinum and it is a commercially available alloy produced to tight thermoelectric property tolerances. These legs 100, 102 are connected to a band electrode 32 formed of substantially pure platinum. For pure platinum band electrodes 32, the following table provides approximate Seebeck coefficients (averaged over the temperature range of from zero to 100° C.) for a variety of different metals and alloys.

| METAL OR ALLOY | SEEBECK COEFFICIENT (mV/C) vs. PURE PLATINUM |
|---|---|
| Bismuth | −0.0734 |
| Constantan | −0.0351 |
| Nickel | −0.0148 |
| Cobalt | −0.0133 |
| Alumel | −0.0129 |
| Mercury | −0.0060 |
| Palladium | −0.0057 |
| Calcium | −0.0051 |
| Gold-chromium | −0.0017 |
| Thorium | −0.0013 |
| Platinum | 0 |
| Alloy 11 | +0.0013 |
| Tantalum | +0.0033 |
| Aluminum | +0.0042 |

-continued

| METAL OR ALLOY | SEEBECK COEFFICIENT (mV/C) vs. PURE PLATINUM |
|---|---|
| Tin | +0.0042 |
| Lead | +0.0044 |
| Magnesium | +0.0044 |
| Stainless Steel, 18-8 | +0.0044 |
| Solder 96.5Sn/3.5Ag | +0.0045 |
| Solder 50Sn/50Pb | +0.0046 |
| Phosphor bronze | +0.0055 |
| Thallium | +0.0058 |
| Yellow brass | +0.0060 |
| Manganin | +0.0061 |
| Iridium | +0.0065 |
| Copper-beryllium | +0.0067 |
| Indium | +0.0069 |
| Rhodium | +0.0070 |
| Silver | +0.0074 |
| Copper | +0.0076 |
| Zinc | +0.0076 |
| Gold | +0.0078 |
| 60Ni/24Fe/16Cr | +0.0085 |
| Cadmium | +0.0090 |
| Tungsten | +0.0112 |
| Cerium | +0.0114 |
| 80Ni/20Cr | +0.0114 |
| Spring steel | +0.0132 |
| Molybdenum | +0.0145 |
| Lithium | +0.0182 |
| Iron | +0.0189 |
| Chromel P | +0.0281 |
| Antimony | +0.0489 |

Thus in accordance with the present invention, the arrangement shown in FIGS. 12 and 13 provides for multiple temperature-sensitive locations, i. e., junctions 104, 106, on the band electrode 32 using only three thermocouple wires 100, 101, 102, as opposed to two thermocouple pairs, i. e., four wires, thus resulting in a considerable saving of space in the ablation catheter.

In FIG. 13, a band electrode 32 is shown having a composition-matched common lead 101 and two sensor leads 100, 102 at the inside surface of the band. Each lead 100, 101 and 102 is separately connected to the band electrode 32 to form the three junctions 104, 105, and 106. Though the two sensor leads 100, 102 may be located anywhere on the band 32 they are preferably positioned approximately 60 degrees apart around the circumference of the band electrode. The common lead 101 may be positioned anywhere on the band electrode 32. In one embodiment (not shown) a separate power lead conducts power to the band electrode 32 to impart ablation energy to the biological target tissue. Thus four leads are used to provide power and to provide temperature sensing in two locations as opposed to five leads which would be required if each thermocouple had two leads.

In a preferred embodiment, the common lead 101 is also used to conduct power to the band electrode 32 to impart ablation energy to the biological target tissue. Thus, in the preferred embodiment only three leads 100, 101, 102 are used to provide power and to sense in two locations at the band electrode 32 rather than five leads as required by an electrode employing conventional thermocouples. This can result in a substantial savings in size because of the existence of fewer leads to be housed by the catheter. In the case of the twelve-band catheter described above in conjunction with FIG. 1, instead of sixty leads, which would be required with two thermocouples per band, each having two leads, and one power lead, only thirty-six leads are required. In a catheter having a thermal sensor on every other band electrode 32 only six of the electrodes require three leads while the remaining six require only one lead, for a total of only twenty-four leads. In either embodiment, there is a substantial decrease in the number of internal components for the catheter.

Because the thermocouple voltages are typically on the order of 0.001 mV to 0.10 mV per degree C., the power conducted on the common lead 101 could interfere with the detection of the temperature-dependent voltages generated at the sensor junctions 104, 106. Filtration could be used to separate the DC thermocouple signals from the drive or power signals. Such an arrangement is shown in FIG. 2.

In another approach, the controller 20 monitors the leads 100, 102 for thermocouple signals only during the off-period 76 of the duty cycle 78, for example, as shown in FIG. 6. During this off-period, no power is being applied to the band electrode 32 over the common electrode lead 101 and there is less chance for interference with the thermocouple signals produced by the band electrode 32 and conducted on both leads 100, 102. Thus, the temperatures may be measured briefly without electrical interference.

It should be appreciated that the invention may also be applied to ablation catheters employing alternate sources of energy for ablation, such as ultrasound or microwave energy. The invention may also be applied to any system in which monitoring temperature is important and where the position of temperature important to the monitoring process.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An apparatus for providing a plurality of signals, each indicative of a temperature at an individual location on an electrode, said apparatus comprising:

an electrode formed of a first metallic material;

a plurality of electrically conductive sensor leads, each individually connected to the electrode to form a sensor junction, each sensor junction having a temperature-dependent voltage associated therewith; and an electrically conductive common lead connected to the electrode to form a common junction, the common lead formed of a second metallic material such that substantially no temperature-dependent voltage is associated with the common junction.

2. The apparatus of claim 1 wherein each of the sensor leads is form of a metallic material different than the first metallic material, each metallic material having a known Seebeck coefficient relative to the first metallic material.

3. The apparatus of claim 2 wherein the ratio of the magnitude of Seebeck coefficient of the sensor lead metallic material relative to the first metallic material and the magnitude of the Seebeck coefficient of the common lead metallic material relative to the first metallic material is at least ten to one.

4. The apparatus of claim 1 wherein the common lead is formed of the first metallic material.

5. The apparatus of claim 1 wherein the first metallic material has an electrical conductivity at least as great as that of platinum/10%iridium.

6. The apparatus of claim 1 wherein the first metallic material is selected from the group consisting of substantially pure silver, gold, chromium, aluminum, molybdenum, tungsten, nickel, and platinum.

7. The apparatus of claim 1 wherein the first metallic material is substantially pure platinum.

8. An apparatus for measuring the temperature at a plurality of locations on an electrode, said apparatus comprising:

an electrode formed of a first metallic material;

a plurality of electrically conductive sensor leads, each individually connected to the electrode to form a sensor junction, each sensor junction having a temperature-dependent voltage associated therewith;

an electrically conductive common lead connected to the electrode to form a common junction, the common lead formed of a second metallic material such that substantially no temperature-dependent voltage is associated with the common junction;

a voltmeter for determining each of the sensor junction temperature-dependent voltages; and a processor for converting each voltage to a temperature value.

9. The apparatus of claim 8 wherein the temperature-dependent voltages are determined by measuring, for each individual sensor lead, the voltage between the sensor lead and the common lead.

10. The apparatus of claim 8 wherein each of the sensor leads is formed of a metallic material different than the first metallic material, each metallic material having a known Seebeck coefficient relative to the first metallic material.

11. The apparatus of claim 10 wherein the ratio of the magnitude of the Seebeck coefficient of the sensor lead metallic material relative to the first metallic material and the magnitude of the Seebeck coefficient of the common lead metallic material relative to the first metallic material is at least ten to one.

12. The apparatus of claim 8 wherein the common lead is formed of the first metallic material.

13. The apparatus of claim 8 wherein the first metallic material has an electrical conductivity at least as great as that of platinum/10%iridium.

14. The apparatus of claim 8 wherein the first metallic material is selected from the group consisting of substantially pure silver, gold, chromium, aluminum, molybdenum, tungsten, nickel, and platinum.

15. The apparatus of claim 8 wherein the first metallic material is substantially pure platinum.

16. A method for monitoring the temperature at a plurality of locations on an electrode, said electrode formed of a first metallic material, said method comprising the steps of:

connecting a plurality of electrically conductive sensor leads to the electrode to form a plurality of sensor junctions, each sensor junction having a temperature-dependent voltage associated therewith;

connecting an electrically conductive common lead connected to the electrode to form a common junction, the common lead formed of a second metallic material such that substantially no temperature-dependent voltage is associated with the common junction;

for each sensor lead, measuring the voltage between the sensor lead and the common lead; and for each measured voltage, converting the measured voltage to a temperature value.

17. The method of claim 16 wherein each of the sensor leads is formed of a metallic material different than the first metallic material, each metallic material having a known Seebeck coefficient relative to the first metallic material.

18. The apparatus of claim 17 wherein the ratio of the magnitude of the Seebeck coefficient of the sensor lead metallic material relative to the first metallic material and the magnitude of the Seebeck coefficient of the common lead metallic material relative to the first metallic material is at least ten to one.

19. The method of claim 16 wherein the common lead is formed of the first metallic material.

20. The method of claim 16 wherein the electrode is a band electrode, there are two sensor junctions and the sensor junctions are located on the band electrode approximately 60° apart around the band electrode circumference.

21. The method of claim 16 wherein the first metallic material has an electrical conductivity at least as great as that of platinum/10%iridium.

22. The method of claim 16 wherein the first metallic material is selected from the group consisting of substantially pure silver, gold, chromium, aluminum, molybdenum, tungsten, nickel, and platinum.

23. The method of claim 16 wherein the electrode is cold worked from the first metallic material so that the electrode has an thermal conductivity substantially the same as that of the first metallic material in raw form and a tensile strength greater than the first metallic material in raw form.

24. The method of claim 23 wherein the first metallic material is at least 50% cold worked.

* * * * *

UNITED STATES PATENT AND TRADEMARK OFFICE
CERTIFICATE OF CORRECTION

PATENT NO.   : 6,309,385 B1
DATED        : October 30, 2001
INVENTOR(S)  : John A. Simpson It is certified that error appears in the above-identified patent and that said Letters Patent is hereby corrected as shown below:

Column 10,
Line 7, add the following:
-- wherein:   $\Delta \varnothing$ = phase angle difference between electrodes.
              V = voltage amplitude of power.
              f = frequency in hertz.
              t = time --.
Line 17, change "8", to read -- 8A --.

Column 12,
Line 29, add the following:
-- wherein:   $\Delta \varnothing$ = phase angle difference between electrodes.
              V = voltage amplitude of power.
              $Z_{e-e}$ = impedance between electrodes.
              f = frequency in hertz.
              t = time --.
Line 37, add the following:
-- wherein:   $\Delta \varnothing$ = phase angle difference between electrodes.
              V = voltage amplitude of power.
              $Z_{e-b}$ = impedance between electrode and backplate.
              f = frequency in hertz.
              t = time --.

UNITED STATES PATENT AND TRADEMARK OFFICE
CERTIFICATE OF CORRECTION

PATENT NO. : 6,309,385 B1
DATED : October 30, 2001
INVENTOR(S) : John A. Simpson It is certified that error appears in the above-identified patent and that said Letters Patent is hereby corrected as shown below:

Column 12,
Line 50, change "9-11", to read -- 9A-11D --.

Column 15,
Line 61, delete duplicated equation.
Line 62, add the following:
-- wherein: $\alpha_{ac}$ = Seebeck coefficient for the first sensor lead 100 material and the band material or for the second sensor lead 102 material and the band material.

$\alpha_{bc}$ = Seebeck coefficient for the common lead 101 material and the band material.

$T_a$ = temperature at the first sensor lead/electrode junction 106.

$T_b$ = temperature at the common lead/electrode junction 105.

$T_{ref}$ = temperature at the reference junction 110. --

Signed and Sealed this

Twentieth Day of August, 2002

Attest:

Attesting Officer

JAMES E. ROGAN
*Director of the United States Patent and Trademark Office*